United States Patent [19]

Barry et al.

[11] Patent Number: 6,081,786
[45] Date of Patent: Jun. 27, 2000

[54] SYSTEMS, METHODS AND COMPUTER PROGRAM PRODUCTS FOR GUIDING THE SELECTION OF THERAPEUTIC TREATMENT REGIMENS

[75] Inventors: David W. Barry, Chapel Hill; Carolyn S. Underwood, Cary; Bruce J. McCreedy, Raleigh; David D. Hadden, Durham, all of N.C.; Jason L. Lucas, West Chester, Pa.

[73] Assignee: Triangle Pharmaceuticals, Inc., Durham, N.C.

[21] Appl. No.: 09/283,702

[22] Filed: Apr. 1, 1999

Related U.S. Application Data

[60] Provisional application No. 60/080,629, Apr. 3, 1998.

[51] Int. Cl.[7] ................................................ G06F 17/60
[52] U.S. Cl. ........................ 705/3; 705/2; 706/45; 706/46; 706/47; 706/924
[58] Field of Search .................. 705/3, 2, 1; 706/45, 706/10, 46, 47, 61, 924

[56] References Cited

U.S. PATENT DOCUMENTS

| | | | |
|---|---|---|---|
| 4,839,822 | 6/1989 | Dormond et al. | 706/45 |
| 4,868,763 | 9/1989 | Masui et al. | 706/10 |
| 5,299,121 | 3/1994 | Brill et al. | 705/2 |
| 5,342,922 | 8/1994 | Marshall et al. | 530/329 |
| 5,355,444 | 10/1994 | Chirico | 706/45 |
| 5,517,405 | 5/1996 | McAndrew | 705/2 |
| 5,594,638 | 1/1997 | Iliff | 705/3 |
| 5,660,176 | 8/1997 | Iliff | 600/300 |
| 5,672,154 | 9/1997 | Sillén et al. | 604/505 |
| 5,694,950 | 12/1997 | McMichael | 128/898 |
| 5,737,539 | 4/1998 | Edelson et al. | 705/3 |
| 5,845,255 | 12/1998 | Mayaud | 705/3 |

(List continued on next page.)

OTHER PUBLICATIONS

Evans et al., *A Computer–Assisted Management Program for Antibiotics and Other Antiinfective Agents*, The N.E. Jour. of Med., vol. 338, No. 4, pp. 232–238 (Jan. 22, 1998).

Abstract, *Infectious Disease Alert*, Am. Health Consul., vol. 17, No. 11, pp. 81–82 (Mar. 1, 1998).

Pazzani et al., *Application of an Expert System in the Management of HIV–Infected Patients*, Jour. of Acq. Immune Def. Syndromes and Human Retrovirology, vol. 15, No. 5, pp. 356–362(1997).

Miller et al., *Summary Recommendations for Responsible Monitoring and Regulation of Clinical Software Systems*, Annals of Internal Medicine, vol. 127, No. 9, pp. 842–845 (Nov. 1, 1997).

Ziporyn, Terra, "Computer–Assisted Medical Decision–Making: Interest Growing", The Journal of the American Medical Association, pp. 913–918, Aug. 27, 1982.

Barnett, G. et al. "DXplain; An Evolving Diagnostic Decision–Support System", The Journal of the American Medical Association, pp. 67–74, Jul. 3, 1987.

(List continued on next page.)

*Primary Examiner*—Emanuel Todd Voeltz
*Assistant Examiner*—John W. Hayes
*Attorney, Agent, or Firm*—Myers Bigel Sibley & Sajovec

[57] ABSTRACT

Systems, methods and computer program products for guiding selection of a therapeutic treatment regimen for a known disease such as HIV infection are disclosed. The method comprises (a) providing patient information to a computing device (the computer device comprising: a first knowledge base comprising a plurality of different therapeutic treatment regimens for the disease; a second knowledge base comprising a plurality of expert rules for selecting a therapeutic treatment regimen for the disease; and a third knowledge base comprising advisory information useful for the treatment of a patient with different constituents of the different therapeutic treatment regimens; and (b) generating in the computing device a listing (preferably a ranked listing) of therapeutic treatment regimens for the patient; and (c) generating in the computing device advisory information for one or more treatment regimens in the listing based on the patient information and the expert rules.

66 Claims, 22 Drawing Sheets

U.S. PATENT DOCUMENTS

| | | | |
|---|---|---|---|
| 5,908,383 | 6/1999 | Brynjestand | 600/300 |
| 5,911,132 | 6/1999 | Sloane | 705/3 |
| 5,924,074 | 7/1999 | Evans | 705/3 |
| 5,950,630 | 9/1999 | Portwood et al. | 705/3 |

OTHER PUBLICATIONS

Wyatt, Jeremy, "Computer–based Knowledge Systems", Lancet, vol. 338, No. 8780, pp. 1431–1437, Dec. 7, 1991.

"UCSF Launches Website 'HIV InSite', A Comprehensive Online gateway to AIDS Knowledge", Business Wire, Dialog File 148:Trade & Industry Database, Mar. 17, 1997.

Evans et al, "A Computer–Assisted Management Program for Antibiotics and Other Antiinfective Agents", The New England Journal of Medicine, vol. 338, No. 4, pp. 232–238, Jan. 22, 1998.

Abstract, "Infectious Disease Alert", American Health Consultants, vol. 17, No. 11, pp. 81–82, Mar. 1, 1998.

Pazzani et al, "Application of an Expert System in the Management of HIV–Infected Patients", Journal of Acquired Immune Deficiency Syndromes and Human Retrovirology, vol. 15, No. 5, pp. 356–362, 1997.

Miller et al, Summary Recommendations for Responsible Monitoring and Regulation of Clinical Software Systems, Annals of Internal Medicine, vol. 127, No. 9, pp. 842–845, Nov. 1, 1997.

International Search Report, PCT Application No. PCT/US99/07171 (Oct. 22, 1999).

| Icon | Meaning |
|---|---|
| ○ | Indicates that there were no critical alerts for the therapy, however, general warnings and advisories should be read in the Therapy Details box. |
| ⟳ | Indicates that there were no critical alerts for the therapy, however, general warnings and advisories should be read in the Therapy Details box. The book indicates that therapy has been studied and a reference is available to review. |
| △ | Indicates a yellow alert. There is important information about this therapy that must be reviewed. |
| ⚠ | Indicates a yellow alert. There is important information about this therapy that must be reviewed. The book indicates that therapy has been studied and a reference is available to review. |
| ! | Indicates a red alert, which means critical and possible life-threatening situation may exist or may be created with this therapy. Information in the Therapy Details section must be read for this therapy to be considered. |
| !▫ | Indicates a red alert, which means critical and possible life-threatening situation may exist or may be created with this therapy. Information in the Therapy Details section must be read for this thereapy to be considered. The book indicates that therapy has been studied and a reference is available to review. |
| X | Indicates the therapy is not recommended. |

FIG. 7.

Therapy Options

| Therapy | Eff. | Adj. | Safety |
|---|---|---|---|
| d4T, 3TC, IDV | 1 | 1 | |
| AZT, 3TC, IDV | 1 | 1 | |
| d4T, 3TC, NFV | 1 | 1 | |
| AZT, 3TC, NFV | 1 | 1 | |

Show Abstract for Retrovir
Show Abstract for Epivir
Show Abstract for Viracept
Show Therapy Study Print Details for AZT, 3TC, NFV
Print Top 10 Therapy Option Details Hide Column "Eff."
Hide Column "Adj."
Hide Column "Safety Considerations"
Show Column "Med"
Show Column "Drug"
Hide Column "Freq."
Hide Column "Pills"
Hide Column "Cost"

Therapy B Evaluated

General

TPMS Patient

Medical History | Chart | Therapy Evaluation

Therapy Being Evaluated: AZT, ddI, RTV, DLV       <Use as Current Therapy | Show Therapies

Recommended Dosages
Retrovir 300mg q 12h (2 pills/day, $9.56/day)
Videx 200mg q 12h (4 pills/day, $6.78/day)
Norvir 600 mg q 12h (12 pills/day, $22.26/day)
Rescriptor 400mg q 8h (12 pills/day, $7.39/day)

Warnings and Side Effects

- AZT: Interrupt Retrovir use if anemia and/or neutropenia develops. More Info 036 DosGenA, Commentary36

- ddI: When treatment with other drugs known to cause pancreatic toxicity is required (for example, IV pentamidine), suspension of Videx should be considered. CmtGenA, Commentary13

- ddI: If patients develop symptoms of neuropathy, Videx therapy should be interrupted. DosGenB, Commentary40

- ddI: Clinical signs suggestive of pancreatitis should prompt dose suspension of Videx and careful evaluation of the possibility of pancreatitis. Only after pancreatitis has been ruled out should dosing be resumed. DosGenB, Commentary39

- DLV: Skin rash attributable to Rescriptor may occur during first 21 days. More Info 054 CmtGenS, Commentary54

Drug Interaction Information

- ddI: Videx should not be administered with a prescription antibiotic containing any form of tetracycline. CmtGenA, Commentary15

- ddI: Plasma concentrations of some quinolone antibiotics are decreased when administered with antacids containing magnesium or aluminum. Therefore, doses of quinolone antibiotics should not be administered within 2 hours of taking Videx. CmtGenA, Commentary16

- RTV: Monitor for decreased AUC of Norvir and associated adverse events when concomitant with use of drugs that increase CYP3A activity (including tobacco). More Info 026 CmtGenH, Commentary26

SYSTEMS, METHODS AND COMPUTER PROGRAM PRODUCTS FOR GUIDING THE SELECTION OF THERAPEUTIC TREATMENT REGIMENS

RELATED APPLICATIONS

This application claims the benefit of U.S. Provisional Application No. 60/080,629 filed Apr. 3, 1998.

A portion of the disclosure of this patent document contains material that is the subject of copyright protection. The copyright owner does not object to the reproduction of the patent disclosure as it appears in the public patent files of the United States Patent and Trademark Office, but otherwise reserves all other rights in the copyrighted material.

FIELD OF THE INVENTION

This invention concerns systems, methods and computer program products for guiding the selection of therapeutic treatment regimens for complex disorders such as cancer and HIV-1 infection, wherein a ranking of available treatment regimens is generated and advisory information clinically useful for treating patients is provided.

BACKGROUND OF THE INVENTION

Therapeutic treatment regimens for disorders such as HIV-1 infection (acquired immune deficiency syndrome or AIDS) and cancer are increasingly complex. New data and new therapeutic treatment regimens continue to modify the treatments available, and it is difficult for all but the specialist to remain current on the latest treatment information. Further, even those who are current on the latest treatment information require time to assimilate that information and understand how it relates to other treatment information in order to provide the best available treatment for a patient. Combination therapeutic treatment regimens exacerbate this problem by making potential drug interactions even more complex. Finally, an increasingly sophisticated patient population, in the face of a vast volume of consumer information on the treatment of disease, makes the mere statement of a treatment regime, without explanation, difficult for the patient to accept.

R. Miller et al., *Summary Recommendations for Responsible Monitoring and Regulation of Clinical Software Systems*, Ann. Intern. Med. 127, 842–845 (1997), describes policy guidelines indicating the desirability of systems that generate advice for clinician users in a manner that users can easily override. Solutions to this need are neither suggested nor disclosed.

M. Pazzani et al., *Application of an Expert System in the Management of HIV-Infected Patients*, J. Acquired Immune Deficiency Syndromes and Human Retrovirology 15, 356–362 (1997) (accepted May 12, 1997), describes a rule-based expert system by which protease, reverse transcriptase, and integrase segments of HIV are cloned and entered into an expert system that recommends two, three, and four drug regimens. A means for easily overriding the advice given is neither suggested nor disclosed.

U.S. Pat. No. 5,672,154 to Sillen describes a method for giving patients individualized, situation-dependent medication advice. The recommended type of medicine may include at least two different medicines. No means for ranking multiple treatment options is disclosed, and no means for explaining why treatment options were rejected is given. Rather, this system is primarily concerned with generating new rules from patient information to optimize a particular therapy for diseases such as Parkinson's disease, epilepsy and abnormal blood pressure.

U.S. Pat. No. 5,694,950 to McMichael describes a method and system for use in treating a patient with immunosuppressants such as cyclosporin. An expert system is employed to generate a recommendation on whether the immunosuppressant dosage should be changed and, if so, how. Ranking or selection among a plurality of different combination therapeutic treatment regimens is not suggested.

U.S. Pat. No. 5,594,638 to Iliff describes a medical diagnostic system that provides medical advice to the general public over a telephone network. This system is not concerned with generating a recommendation for a combination therapeutic treatment regimen for a known disease (see also U.S. Pat. No. 5,660,176 to Iliff).

SUMMARY OF THE INVENTION

In view of the foregoing, an object of the invention is to provide systems, methods and computer program products for selecting therapeutic treatment regimens for patients in which available treatments are listed, and optionally ranked, while unavailable or rejected treatment regimens (e.g., regimens that would not be effective, or would be dangerous) are not displayed or are assigned a low rank and are indicated to a user as not likely to be efficacious, or not preferred due to patient-specific complicating factors such as drug interaction from concomitant medications.

A further object of the invention is to provide systems, methods and computer program products for selecting treatment regimens in which the available treatment options can be readily understood.

A further object of the invention is to provide systems, methods and computer program products for selecting treatment regimens in which the implications of selecting a particular treatment regimen can be readily understood.

A further object of the invention is to provide systems, methods and computer program products for selecting treatment regimens in which the reasons for rejection of a particular regimen can be readily understood.

A still further object of the invention is to provide systems, methods and computer program products for obtaining information about the efficacy of previous treatment regimens imposed on patients.

A method of the present invention includes providing patient information to a computing device that includes various knowledge bases. For example, a first knowledge base may include a plurality of different therapeutic treatment regimens for a disease or medical condition. A second knowledge base may include a plurality of expert rules for selecting a therapeutic treatment regimen for the disease or medical condition. A third knowledge base may include advisory information useful for the treatment of a patient with different constituents of different therapeutic treatment regimens. A fourth knowledge base may include information about past therapies, such as how a patient has fared under previous therapies.

A listing (preferably a ranked listing) of therapeutic treatment regimens for a patient is generated in the computing device. Advisory information for one or more treatment regimens in the listing is generated in the computing device based on the patient information and the expert rules.

In a preferred embodiment, the method described above further includes entering a user-defined therapeutic treatment regimen for the disease (or medical condition) that may not be displayed from the system knowledge base-generated therapeutic treatment regimens, and generating in the computing device advisory information for the user-defined combination therapeutic treatment regimen.

In addition, in a preferred embodiment, the method described above further includes entering a rejected therapeutic treatment regimen for the disease (or medical condition) that is included in the first knowledge base but not recommended from the ranking (or given a very low ranking), and generating in the computing device advisory information for the non-recommended/low ranked therapeutic treatment regimen, wherein the advisory information includes at least one reason for not recommending (or low ranking) the therapeutic treatment regimen.

Further objects and aspects of the present invention are explained in detail in the drawings herein and the specification set forth below.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 4 illustrates a medical history user interface for entering data about a patient's medical history according to the present invention.

FIG. 7 illustrates various symbols for providing information about a therapeutic treatment regimen option within the therapy list box of the therapy evaluation user interface of FIG. 6 according to the present invention.

FIG. 9 illustrates a pop-up menu including an indexed electronic link to a PDR® that can be activated from within the therapy list box of the therapy evaluation user interface of FIG. 6 according to the present invention.

FIGS. 11A–11E illustrate various functions of the present invention as described in Example 2.

FIGS. 12A–12C illustrate various functions of the present invention as described in Example 3.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

As will be appreciated by one of skill in the art, the present invention may be embodied as a method, data processing system, or computer program product. Accordingly, the present invention may take the form of an entirely hardware embodiment, an entirely software embodiment, or an embodiment combining software and hardware aspects. Furthermore, the present invention may take the form of a computer program product on a computer-usable storage medium having computer readable program code means embodied in the medium. Any suitable computer readable medium may be utilized including, but not limited to, hard disks, CD-ROMs, optical storage devices, and magnetic storage devices.

The present invention is described below with reference to flowchart illustrations of methods, apparatus (systems), and computer program products according to an embodiment of the invention. It will be understood that each block of the flowchart illustrations, and combinations of blocks in the flowchart illustrations, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Figure 1:
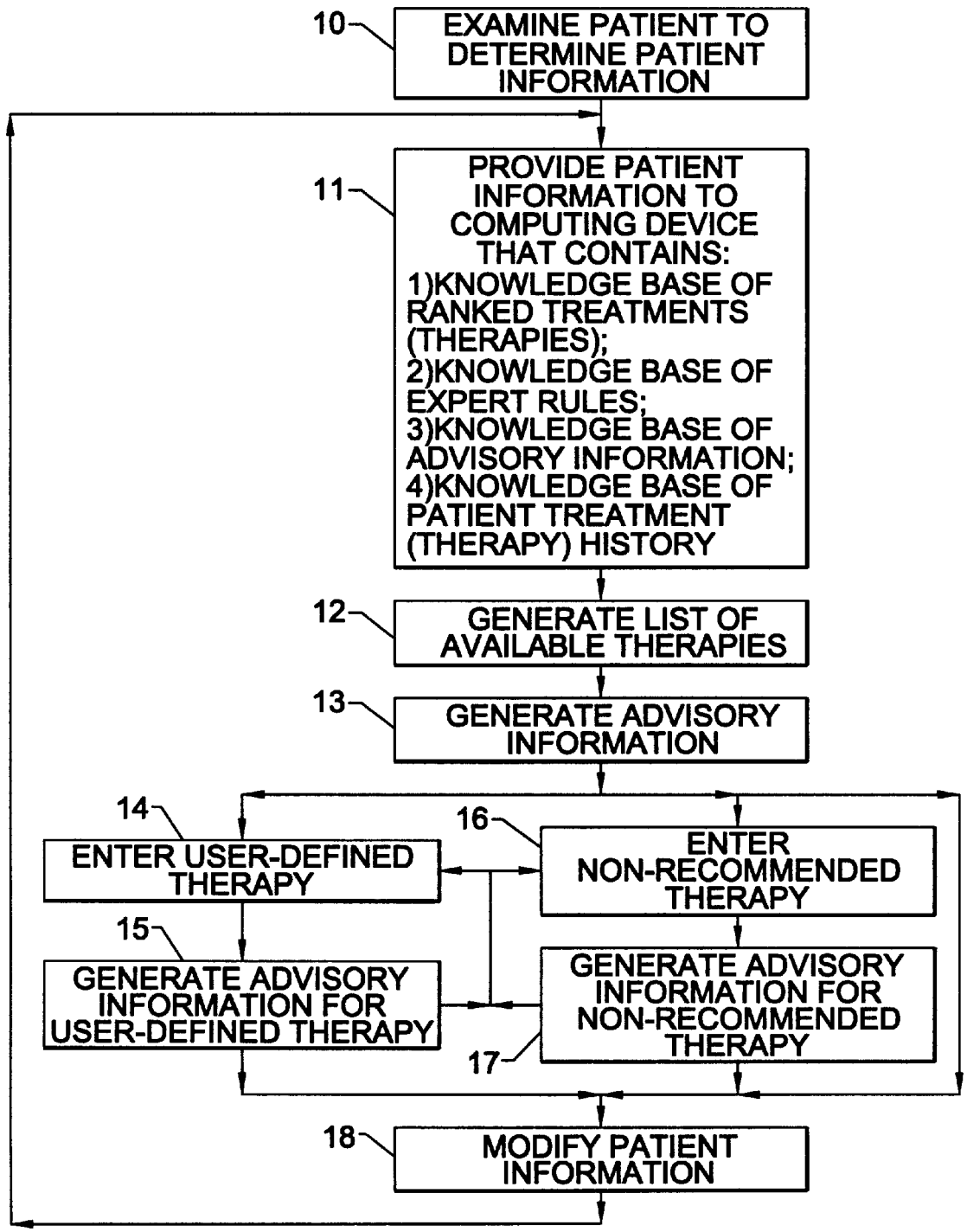
FIG. 1 illustrates a process of the instant invention, including routines for entering a user-defined therapeutic treatment regimen and for entering a "non-recommended" therapeutic treatment regimen.

A method of the instant invention is illustrated in FIG. 1. In the first step 10, the patient is examined to determine patient information. Examples of patient information that may be gathered include one or more of gender, age, weight, $CD4^+$ cell information, viral load information, HIV genotype and phenotype information, hemoglobin information, neuropathy information, neutrophil information, pancreatitis, hepatic function, renal function, drug allergy and intolerance information, and information for drug treatments for other conditions. The information may include historical information on prior therapeutic treatment regimens for the disease or medical condition. While the patient is typically examined on a first visit to determine the patient information, it will be appreciated that patient information may also be stored in the computing device, or transferred to the computing device from another computing device, storage device, or hard copy, when the information has been previously determined.

The patient information is then provided 11 to a computing device that contains a knowledge base of treatments, contains a knowledge base of expert rules for determining available treatment options for the patient in light of the patient information, and also contains a knowledge base of advisory information. A list of available treatments for the patient is then generated 12 from the patient information and the available treatments by the expert rules, and advisory information for the available treatments is generated 13. The advisory information may include warnings to take the patient off a contraindicated drug or select a suitable non contraindicated drug to treat the condition before initiating a corresponding treatment regimen and/or information clinically useful to implement a corresponding therapeutic treatment regimen.

For example, when the known disease is HIV-1 infection, the treatment regimen includes antiretroviral drugs, and the treatment regimen or advisory information may also include contraindicated or potentially adversely interacting non-antiretroviral drugs. Particularly, when the treatment regimen includes a protease inhibitor. A contraindicated drug may be terfenadine. When the treatment regimen includes indinavir, a contraindicated drug is cisapride.

Exemplary antiretroviral drugs are listed below in Table 1.

TABLE 1

| Abbreviation | Formal Name | Generic Name |
| --- | --- | --- |
| ABC | ZIAGEN ® | Abacavir |
| ADV | PREVEON ® | Adefovir |
| APV | AGENERASE ® | Amprenavir |
| AZT | RETROVIR ® | Zidovudine |
| ddI | VIDEX ® | Didanosine |
| ddC | HIVID ® | Zalcitabine |
| d4T | ZERIT ® | Stavudine |
| EFV | SUSTIVA ® | Efavirenz |
| 3TC | EPIVIR ® | Lamivudine |
| SQV | INVIRASE ® FORTOVASE ® | Saquinavir |
| IDV | CRIXIVAN ® | Indinavir |
| RTV | NORVIR ® | Ritonavir |
| DLV | RESCRIPTOR ® | Delavirdine |
| NFV | VIRACEPT ® | Nelfinavir |
| NVP | VIRAMUNE ® | Nevirapine |

Exemplary advisory information that can be displayed to a user is summarized below in Table 2.

TABLE 2

| | Description |
| --- | --- |
| Drug Therapies (All the output data types below are associated with a therapy) | The inference engine will process every therapy from a resource file which contains all valid therapy combinations. The system will support multiple drug combinations. Those therapies which are recommended by the knowledge base will be displayed along with all the data types below. |
| Commentaries | Commentaries consist of warnings and advisories concerning drugs as well as various patient conditions. Each commentary will appear in specific locations of the User Interface. Commentaries will have various Flags, Triggers, and Output Locations. |

TABLE 2-continued

| | Description |
| --- | --- |
| Rejection Notices | Rejection Notices are the explanation why a given therapy is not recommended. Rejection notices always appear in predefined places in the User Interface. |
| Cost | The cost per day is calculated for each therapy by the inference engine as well as each drug cost within a therapy. |
| Dosage | The base dosage and any adjustments to the base dosage due to various patient conditions are calculated by the inference engine. |
| Pill Burden | The number of pills in the therapy. |
| Frequency | Number of times the patient will be taking medications for a given therapy. For a multi-drug therapy, the Frequency of the therapy is the drug in the therapy that has the highest number of Frequencies. If a three-drug regimen has 2 drugs with q12h dosages and one that is a q8h, the therapy is considered to be a q8h Frequency. |
| Admin | Special drug administration instructions. |
| Efficacy | The relative Efficacy is a whole number that represents the relative efficacy of the various therapies. One is the most effective therapy. |
| Adjusted Score | The "Adjusted Score" is the Efficacy adjusted up or down based on patient specific characteristics to roughly indicate the likelihood of that therapy being an effective treatment for that patient. An example would be: the system evaluates a therapy containing a drug that is known to be associated with a medical condition in that patient's medical history, therefore the therapy is ranked low. The Ranking Ordinal is an integer, beginning with 0 and having no upper limit. A therapy with a 1 Ranking Ordinal (RO = 1) would be ranked at the top of the list whereas a therapy with a 10 Ranking Ordinal (RO = 10) would be less likely to be successful given the patient's specific history and characteristics. Each therapy will have a starting RO number which will be the therapy's relative efficacy score. The relative efficacy score can then be adjusted up or down by the rules. Both base "Efficacy" number and the "Adjusted Score" number can be displayed. |

Diseases (or medical conditions), the treatment of which may be facilitated or improved by the present invention, are those for which multiple different therapy options are available for selection and treatment. Such diseases and medical conditions include, but are not limited to, cardiovascular disease (including but not limited to congestive heart failure, hypertension, hyperlipidemia and angina), pulmonary disease (including but not limited to chronic obstructive pulmonary disease, asthma, pneumonia, cystic fibrosis, and tuberculosis), neurologic disease (including but not limited to Alzheimer's disease, Parkinson's disease, epilepsy, multiple sclerosis, amyotrophic lateral sclerosis or ALS, psychoses such as schizophrenia and organic brain syndrome, neuroses, including anxiety, depression and bipolar disorder), hepatitis infections (including hepatitis B and hepatitis C infection), urinary tract infections, venereal disease, cancer (including but not limited to breast, lung, prostate, and colon cancer), etc. It should be appreciated that prevention of development or onset of the above-mentioned diseases and medical conditions may be facilitated or improved by the present invention.

The present invention is useful for known diseases such as HIV-1 infection (acquired immune deficiency syndrome or "AIDS"), or where the known disease is any medical condition for which a combination therapeutic treatment regimen can be used. The invention is particularly useful when the list of available treatments includes a plurality (e.g., 2, 10 or 15 or more) of treatment, combination therapeutic treatment regimens (e.g., therapeutic treatment regimens incorporating two or more active therapeutic agents), where the potential for drug interactions is increased and/or the complexity involved in selecting the best available treatment is multifactorial.

Advantageously, the list of available treatments and advisory information may be regenerated in a number of ways. The patient information may be simply modified 18. In addition, if a particular therapy in which the user might be interested is not presented, a user-defined therapy may be entered 14 and advisory information generated 15 based on the user-defined therapy. Still further, if a therapeutic treatment regimen that is in the knowledge base is rejected by the system (not recommended upon display), the non-recommended therapeutic treatment regimen may be entered 16 and advisory information generated 17 for the non-recommended therapeutic treatment regimen. This may indicate to the user that they should discontinue use of a non-critical drug for another condition or select a suitable substitute that does not create a conflict/non-recommended situation so that they can then proceed with the therapy of choice. Alternatively, the advisory information can be generated automatically for non-recommended therapeutic treatment regimens. These various steps can be repeated in any sequence in an interactive manner to provide the user with assurance that all treatment options have been given adequate and appropriate consideration.

The terms "therapy" and "therapeutic treatment regimen" are interchangeable herein and, as used herein, mean any pharmaceutical or drug therapy, regardless of the route of delivery (e.g., oral, intraveneous, intramuscular, subcutaneous, intraarterial, intraperitoneal, intrathecal, etc.), for any disease (including both chronic and acute medical conditions, disorders, and the like). In addition, it is understood that the present invention is not limited to facilitating or improving the treatment of diseases. The present invention may be utilized to facilitate or improve the treatment of patients having various medical conditions, without limitation.

System Description

The present invention may be embodied as an expert system that provides decision support to physicians (or other health care providers) treating patients with a known disease, such as HIV infection. A system according to the present invention calculates combination antiretroviral therapy options and attaches all relevant information to those options.

As known to those of skill in the art, an expert system, also known as artificial intelligence (AI), is a computer program that can simulate the judgment and behavior of a human or an organization that has expert knowledge and experience in a particular field. An expert system typically contains a knowledge base containing accumulated experience and a set of rules for applying the knowledge base to each particular situation that is described to the program. Expert systems are well known to those of skill in the art and need not be described further herein.

The antiretroviral therapy options (combinations of antiretroviral drugs), are derived using a knowledge base consisting of a number of expert system rules and functions which in turn take into account a given patient's treatment history, current condition and laboratory values. A system according to the present invention supports the entry, storage, and analysis of patient data in a large central database. A system according to the present invention has a flexible data driven architecture and custom reporting capabilities designed to support patient therapy management and clinical drug trial activities such as screening, patient tracking and support. It is anticipated that a system according to the present invention may be used by health care providers (including physicians), clinical research scientists, and possibly healthcare organizations seeking to find the most cost-effective treatment options for patients while providing the highest standard of care.

Figure 2:
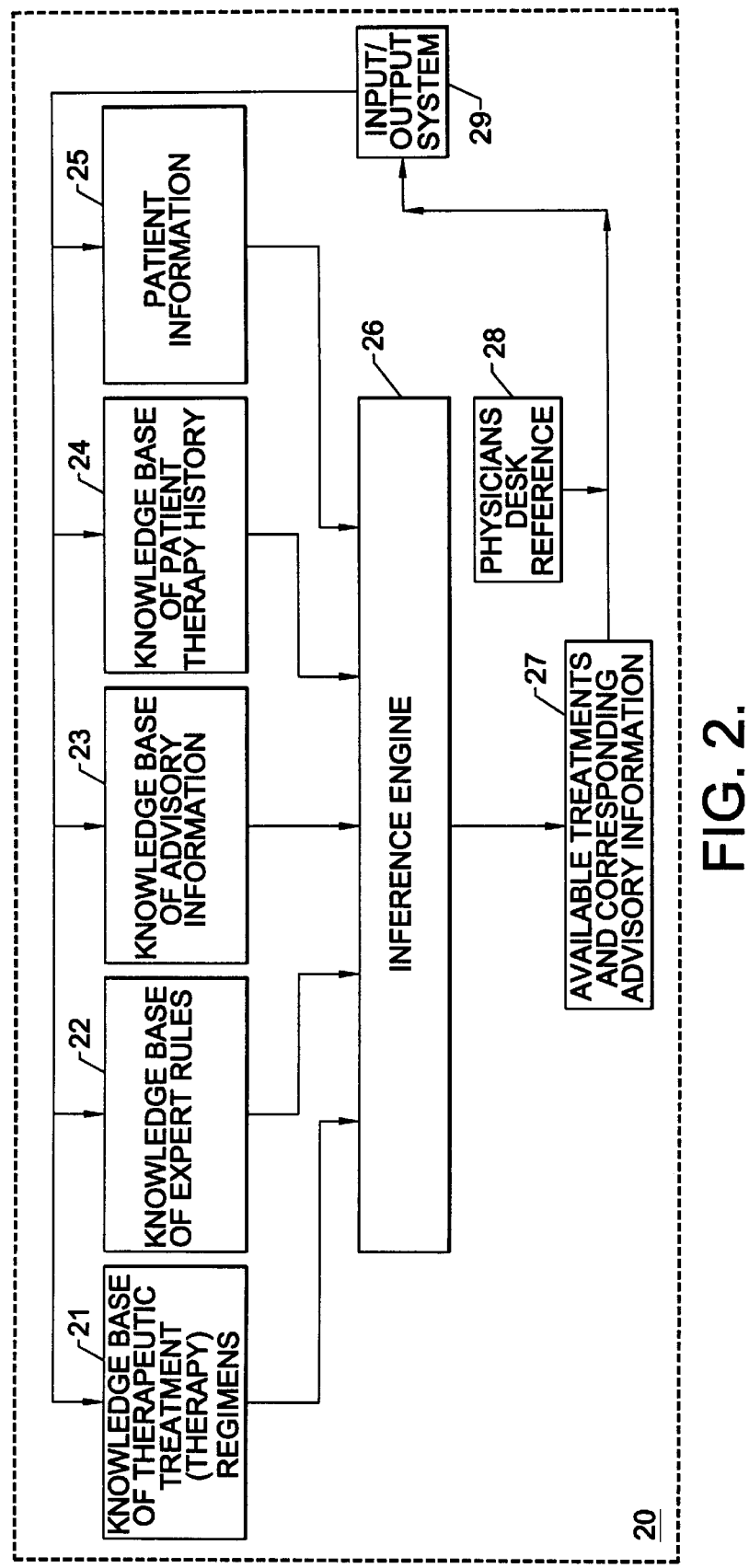
FIG. 2 schematically illustrates a system or apparatus of the present invention.

A system 20 for carrying out the present invention is schematically illustrated in FIG. 2. The system 20 comprises a knowledge base of treatment regimens 21, which may be ranked for efficacy (e.g., by a panel of experts) or ranked according to system rules, a knowledge base of expert rules 22, a knowledge base of advisory information 23, a knowledge base of patient therapy history 24 and patient information 25. Patient information is preferably stored within a database and is configured to be updated. The knowledge bases and patient information 21–25 may be updated by an input/output system 29, which can comprise a keyboard (and/or mouse) and video monitor. Note also that, while the knowledge bases and patient data 21–25 are shown as separate blocks, the knowledge bases and patient data 21–25 can be combined together (e.g., the expert rules and the advisory information can be combined in a single database).

To carry out the method described above, the information from blocks 21–25 is provided to an inference engine 26, which generates the listing of available treatments and the corresponding advisory information from the information provided by blocks 21–25. The inference engine 26 may be implemented as hardware, software, or combinations thereof. Inference engines are known and any of a variety thereof may be used to carry out the present invention. Examples include, but are not limited to, those described in U.S. Pat. No. 5,263,127 to Barabash et al. (Method for fast rule execution of expert systems); U.S. Pat. No. 5,720,009 to Kirk et al. (Method of rule execution in an expert system using equivalence classes to group database objects); U.S. Pat. No. 5,642,471 to Paillet (Production rule filter mechanism and inference engine for expert system); U.S. Pat. No. 5,664,062 to Kim (High performance max-min circuit for a fuzzy inference engine).

High-speed inference engines are preferred so that the results of data entered are continually updated as new data is entered. As with the knowledge bases and patient information in blocks 21–25, the inference engine 26 may be a separate block from the knowledge bases and patient information blocks 21–25, or may be combined together in a common program or routine.

Note that the advisory information that is generated for any available therapy may differ from instance to instance based on differences in the patient information provided.

System Architecture

The present invention can be implemented as a system running on a stand alone computing device. Preferably, the present invention is implemented as a system in a client-server environment. As is known to those of skill in the art, a client application is the requesting program in a client-server relationship. A server application is a program that awaits and fulfills requests from client programs in the same or other computers. Client-server environments may include public networks, such as the Internet, and private networks often referred to as "intranets", local area networks (LANs) and wide area networks (WANs), virtual private networks (VPNs), frame relay or direct telephone connections. It is understood that a client application or server application, including computers hosting client and server applications, or other apparatus configured to execute program code embodied within computer usable media, operates as means for performing the various functions and carries out the methods of the various operations of the present invention.

Figure 3:
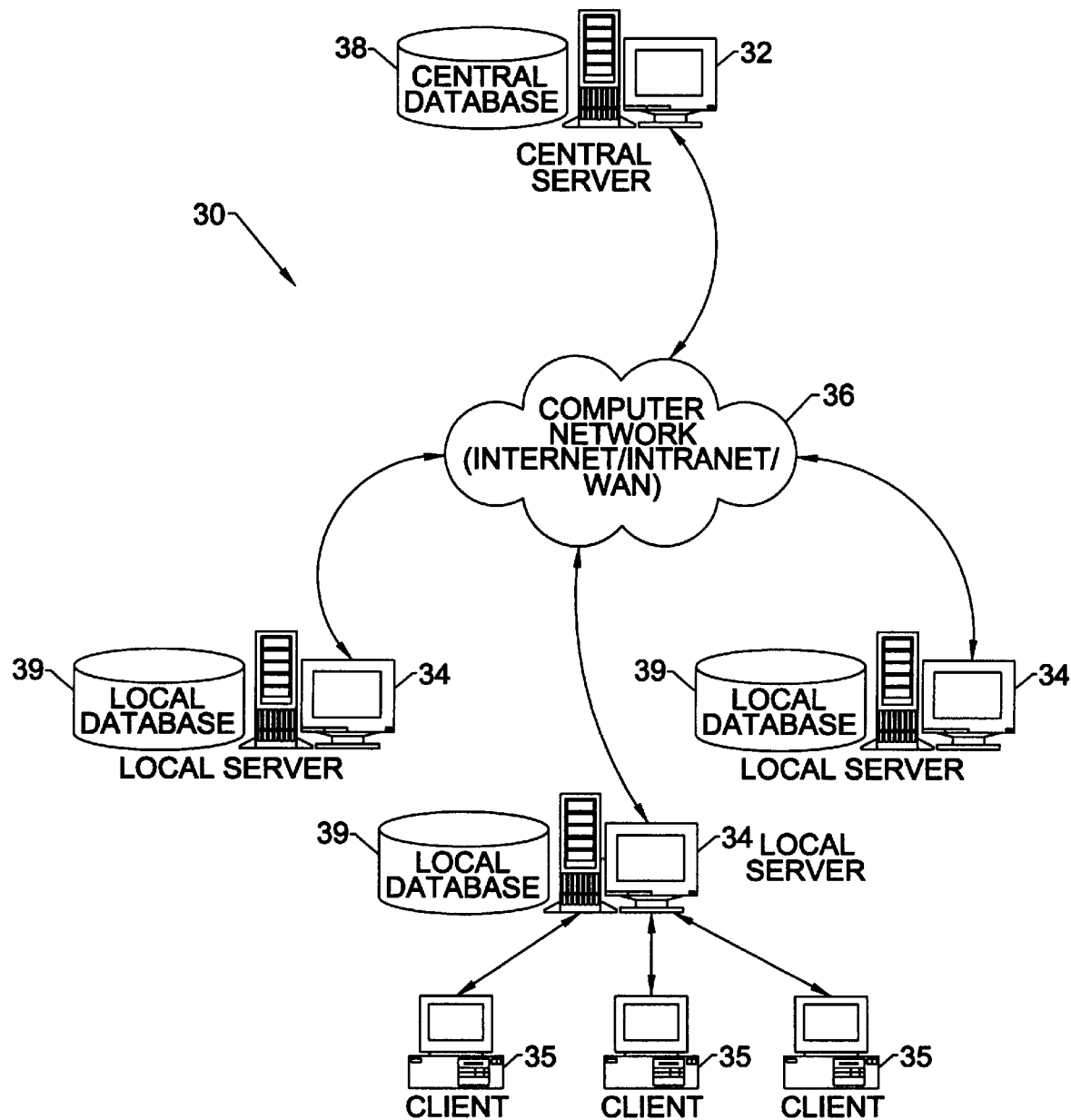
FIG. 3 illustrates a client-server environment within which the system of FIG. 2 may operate, according to an embodiment of the present invention, and wherein a central server is accessible by at least one local server via a computer network, such as the Internet, and wherein each local server is accessible by at least one client.

Referring now to FIG. 3, a client-server environment 30 according to a preferred embodiment of the present invention is illustrated. The illustrated client-server environment 30 includes a central server 32 that is accessible by at least one local server 34 via a computer network 36, such as the Internet. A variety of computer network transport protocols including, but not limited to TCP/IP, can be utilized for communicating between the central server 32 and the local servers 34.

Central Server

The central server 32 includes a central database 38, such as the Microsoft® SQL Server application program, version 6.5 (available from Microsoft, Inc., Redmond, Wash.), executing thereon. The central server 32 ensures that the local servers 34 are running the most recent version of a knowledge base. The central server 32 also stores all patient data and performs various administrative functions including adding and deleting local servers and users to the system (20, FIG. 2). The central server 32 also provides authorization before a local server 34 can be utilized by a user. Patient data is preferably stored on the central server 32, thereby providing a central repository of patient data. However, it is understood that patient data can be stored on a local server 34 or on local storage media.

Local Server

Each local server 34 typically serves multiple users in a geographical location. Each local server 34 includes a server application, an inference engine, one or more knowledge bases, and a local database 39. Each local server 34 performs artificial intelligence processing for carrying out operations of the present invention. When a user logs on to a local server 34 via a client 35, the user is preferably authenticated via an identification and password, as would be understood by those skilled in the art. Once authenticated, a user is permitted access to the system (20, FIG. 2) and certain administrative privileges are assigned to the user.

Each local server 34 also communicates with the central server 32 to verify that the most up-to-date version of the knowledge base(s) and application are running on the requesting local server 34. If not, the requesting local server 34 downloads from the central server 32 the latest validated knowledge base(s) and/or application before a user session is established. Once a user has logged onto the system (20, FIG. 2) and has established a user session, all data and artificial intelligence processing is preferably performed on a local server 34. An advantage of the illustrated client-server configuration is that most of the computationally intensive work occurs on a local server 34, thereby allowing "thin" clients 35 (i.e., computing devices having minimal hardware) and optimizing system speed.

In a preferred embodiment, each local server database 39 is implemented via a Microsoft® SQL Server application program, Version 6.5. The primary purpose of each local database 39 is to store various patient identifiers and to ensure secure and authorized access to the system (20, FIG. 2) by a user. It is to be understood, however, that both central and local databases 38, 39 may be hosted on the central server 32.

Local Client

Each local client 35 also includes a client application program that consists of a graphical user interface (GUI) and a middle layer program that communicates with a local server 34. Program code for the client application program may execute entirely on a local client 35, or it may execute partly on a local client 35 and partly on a local server 34. As will be described below, a user interacts with the system (20, FIG. 2) by entering (or accessing) patient data within a GUI displayed within the client 35. The client 35 then communicates with a local server 34 for analysis of the displayed patient information.

Computer program code for carrying out operations of the present invention is preferably written in an object oriented programming language such as JAVA®, Smalltalk, or C++. However, the computer program code for carrying out operations of the present invention may also be written in conventional procedural programming languages, such as the "C" programming language, in an interpreted scripting language, such as Perl, or in a functional (or fourth generation) programming language such as Lisp, SML, or Forth.

The middle layer program of the client application includes an inference engine within a local server 34 that provides continuous on-line direction to users, and can instantly warn a user when a patient is assigned drugs or a medical condition that is contraindicated with, or antagonistic of, the patient's current antiretroviral therapy. Every time patient data is entered into the system (20, FIG. 2) or updated, or even as time passes, the inference engine evaluates the current status of the patient data, sorting, categorizing, ranking and customizing every possible antiretroviral therapy for a patient according to the specific needs of the patient.

Inference Engine

Inference engines are well known by those of skill in the art and need not be described further herein. Each knowledge base used by an inference engine according to the present invention is a collection of rules and methods authored by a clinical advisory panel of HIV-treating physicians and scientists. A knowledge base may have subjective rules, objective rules, and system-generated rules. Objective rules are based on industry established facts regarding the treatment of HIV using antiretroviral therapy and are drawn from the package insert information of antiretroviral drug manufacturers and from peer reviewed and published journal articles. An example of an objective rule would be an antiretroviral to antiretroviral contraindication such as:

Rule #1: If the eval therapy contains Zidovudine (AZT) and Stavudine (d4T), then reject the therapy.

In Rule #1, the term "eval therapy" refers to the therapy currently being analyzed by the system (20, FIG. 2). Rule #1 then states that if this therapy contains both AZT and d4T, then this therapy should not be displayed in a list of potential therapy options for the patient.

For objective rules, the present invention can be configured so as to prevent a user from receiving recommendations on new therapy options when certain crucial data on the patient has not been entered. However, it is understood that the present invention does not prevent a health care provider, such as a physician, from recording his/her therapy decisions, even if the system (20, FIG. 2) has shown reasons why that therapy may be harmful to the patient. The present invention allows a health care provider to be the final authority regarding patient therapy.

Subjective rules are based on expert opinions, observations and experience. Subjective rules are typically developed from "best practices" information based on consensus opinion of experts in the field. Such expert opinion may be based on knowledge of the literature published or presented in the field or their own experience from clinical practice, research or clinical trials of approved and unapproved medications. A number of experts are used so that personal bias is reduced.

System generated rules are those derived from the outcomes of patients tracked in the system who received known and defined therapies and either improved, stabilized or worsened during a defined period. Because of the large number of potential combinations usable in HIV infection, this system generated database and rules derived from them are likely to encompass data beyond that achievable from objective or subjective rules databases.

The rules which comprise the various knowledge bases (21–24, FIG. 2) of the present invention each have two main parts: a premise and a conclusion—also referred to as the left side and the right side, respectively. When a premise of a rule is found to be true, the action specified in the conclusion is taken. This is known to those of skill in the art as "firing" the rule. For example, consider the following rule:

| Rule ID | Premise | Conclusion |
| --- | --- | --- |
| FiltDComA1 - - | If the eval therapy contains ddC - | Commentary 18 |

The premise of the above rule is for the inference engine to determine whether or not a therapy being evaluated (i.e., "eval therapy" ) contains the antiretroviral drug "ddC" . If a therapy does contain the antiretroviral drug ddC, the action called for by the conclusion of the rule is to attach "Commentary 18" to the therapy. Commentary 18 may be a piece of text that provides a user with the necessary information about therapies containing ddC.

Exemplary rules which may comprise one or more knowledge bases according to the present invention are listed below in Table 3.

TABLE 3

Therapy initiation/change: Rules that provide information on therapy change or initiation
Boundary condition rules: Limits for values, intervals for values to be updated
Comment Data Aging rules: These rules warn the user that the data in certain fields is getting old and that the most current values in the system will be used.
Rules that filter therapies due to drug interactions in ARV drug combinations
Rules that filter therapies due to medical conditions
Rules that filter therapies due to genotypic mutations in patient's plasma HIV
Rules that filter therapies due to phenotypic sensitivity/resistance
Antiretroviral therapy ranking rules
General dosage rules
Solid dosage rule
Dosage modifications due to ARV-ARV drug combination
Dosage modification due to ARV-NonARV interaction
Dosage modification due to medical condition
Comment determined
General commentary rules
Commentaries added due to medical conditions
Commentaries added due to drug interactions
Commentaries added due to drug combination
Delivery size rules Using the various knowledge bases and patient information of the present invention (21–25, FIG. 2), the inference engine (26, FIG. 2) can evaluate potential therapy options for a patient based on a patient's medical history (including therapy history) and current laboratory values. Accordingly multiple antiretroviral drug combinations can be quickly and accurately analyzed for a particular patient. Furthermore, the inference engine can quickly provide guidance in the areas listed below in Table 4.

TABLE 4

| | |
| --- | --- |
| Data Integrity | Is the patient lab and assessment data getting too old to be considered reliable? Are there conflicts between lab data such as phenotype data which indicates resistance to one or more antiretroviral drugs in the patient's current therapy and current viral load data which indicates significant viral suppression? |
| Therapy Performance | Should antiretroviral therapy be initiated for the patient? Is the patient's current therapy achieving good initial and long-term viral suppression or should the therapy be changed? Are there potential non-compliance issues as demonstrated by a lack of viral suppression with a regimen when current genotype or phenotype data does provide explanation for the failure by demonstrating resistance to any drugs in the patient current therapy? |
| Dosage | What are the base and adjusted dosages of antiretroviral drugs in a given therapy? Are there any special specific dosage administration instructions? What are options if patient can only take liquid dosage forms? |
| Contra-indications | Which antiretroviral drugs can be used with each other and what dosage adjustments are required? Are there any contraindications or interactions between antiretroviral drugs in patient's current therapy or potential therapies and the non-antiretroviral drugs patient is taking and if so what are they and what, if any, dosage adjustments are required? |
| Medical Conditions | Are there any medical conditions to be aware of in deciding an appropriate therapy for patient? What, if any, effect do current or historical medical conditions have on each therapy option? |
| Drug Cost and Delivery Data | How much does each therapy option cost? What is the dosing frequency of the drugs in the therapy? What is the pill count and optimum delivery size for the least number of pills? |
| Therapy Options | What are all the drug combination therapy options for patient? How can physician instantly assess which of the hundreds of potential combinations will be the most effective for patient? What information from the package inserts from each drug apply specifically to patient? What is the relative antiviral efficacy of each therapy? Are there special considerations that might make one therapy more or effective for patient? |
| Resistance | What drugs are patient's virus current genotypic or phenotypic profile known to be associated with resistance to? Which antiretroviral drugs are more effective against resistant strains when used together? Which drugs (if any) used in historical therapies are most likely to be effective if recycled into a new therapy? Can any of the drugs in patient's current therapy be recycled into the next therapy? |

User Interface

Figure 4:
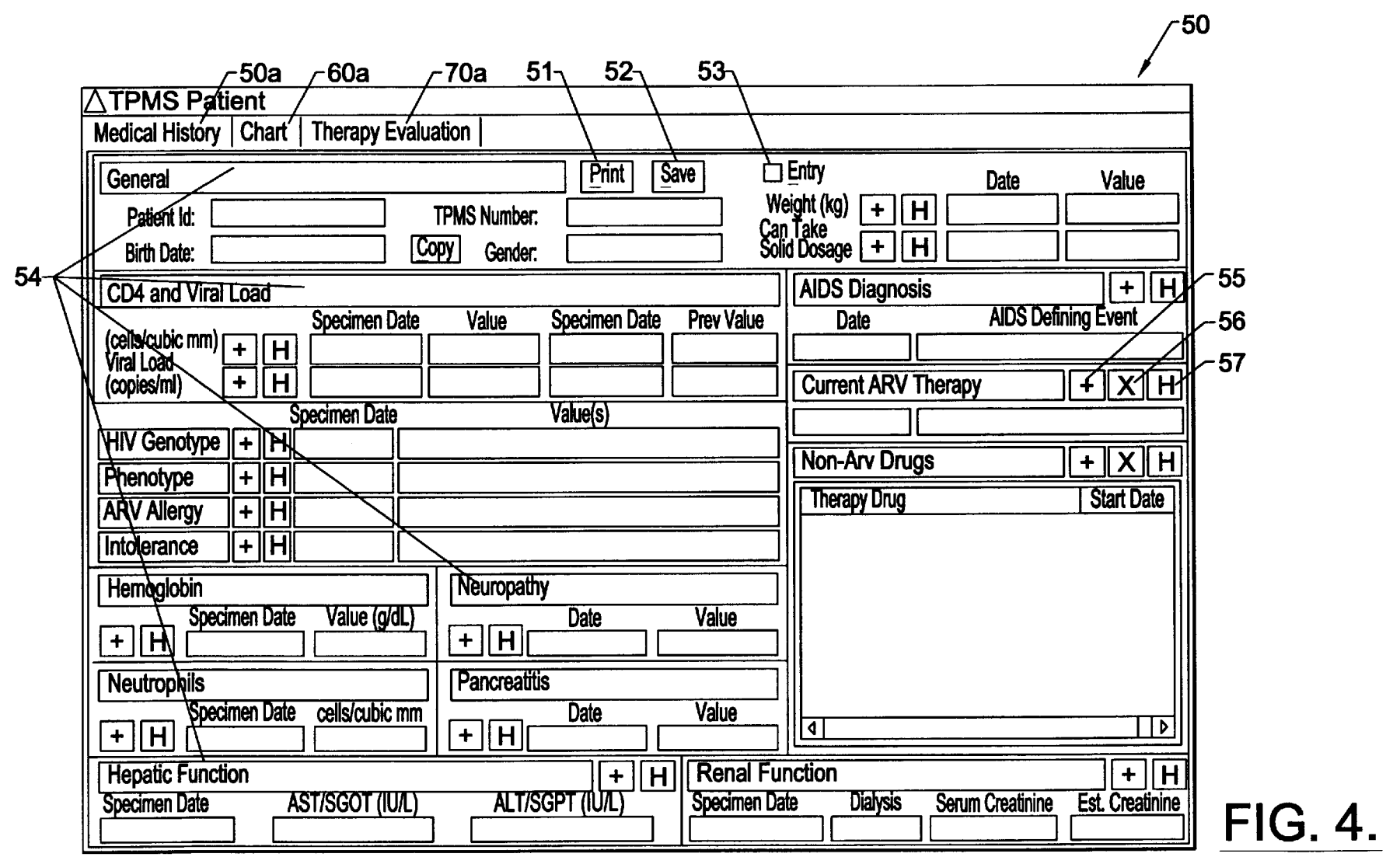

Referring now to FIGS. 4–9, exemplary user interfaces according to the present invention will be illustrated. In FIG. 4, a medical history user interface 50 for entering data about a patient's medical history according to the present invention is illustrated. The medical history user interface 50 can be displayed by activating the "Medical History" tab 50a. The illustrated medical history user interface 50 allows a user to create, save, update and print patient records. When a user adds a new patient, the medical history user interface 50 appears with empty data entry fields. Data entry fields for receiving information via a GUI are well known to those of skill in the art and need not be described further herein. When a user opens a patient record for editing, the medical history user interface 50 appears with patient data in the various fields. Preferably color is used to highlight critical or required information in a patient record.

Important elements in the illustrated medical history user interface 50 include a "print" button 51 for printing a patient record and therapeutic treatment regimen details; a "save" button 52 for saving a patient record; and a "speed entry" check box 53 for allowing a user to move quickly between entry fields. In addition, there are multiple group headings 54 that divide a patient's medical history into related categories. Each group contains entry fields in which a user can add patient information. An "add" button 55 allows a user to add new information to a patient record for a selected group. A "delete" button 56 allows a user to delete patient information for a selected group (although the original information is still recorded in the database). A "history" button 57 allows a user to review a patient's historical data for each selected group.

After completing a patient's medical history, an inference engine analyzes the data and suggests whether a therapeutic treatment regimen is indicated; if an existing therapeutic treatment regimen should be continued or changed; and the best drug therapies for the selected patient. Often, more than one drug therapy is presented to the user. These drug therapies are preferably ranked according to expected efficacy, frequency in dosage, pill count, and cost. All of these factors can help the user make a decision about what therapy to use for the selected patient. When a user clicks on a drug therapy in the presented list, information is provided about the dosage regimens. Also, various warnings, such as drug interaction warnings, and notes about each drug, are presented. An appropriate drug therapy can then be selected.

Figure 5:
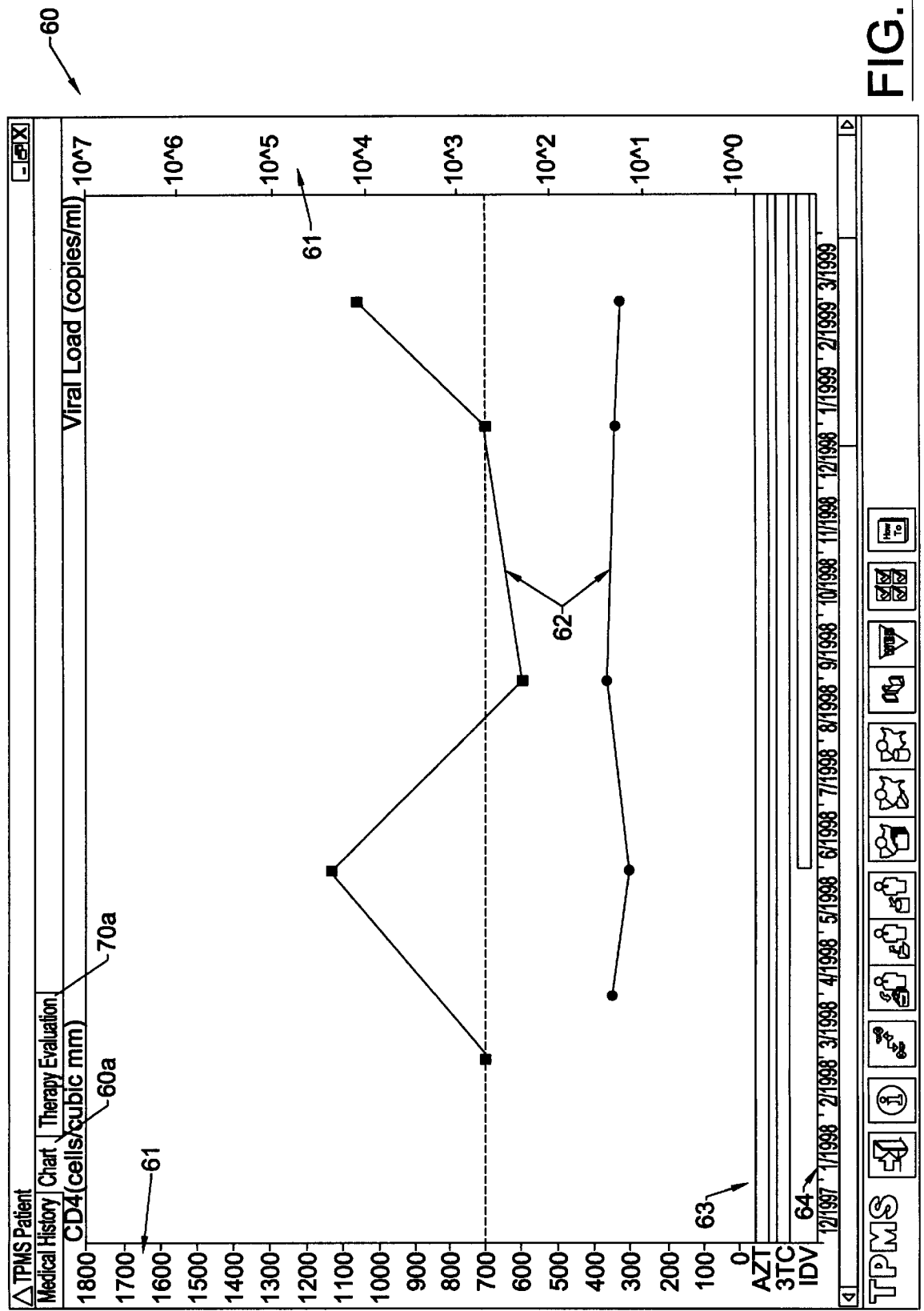
FIG. 5 illustrate a user interface chart for monitoring a patient's condition during a particular therapeutic treatment regimen over a period of time according to the present invention.

In FIG. 5, an exemplary user interface chart 60 for monitoring a patient's condition during a particular drug therapy over a period of time is illustrated. The user interface chart 60 can be displayed by activating the "Chart" tab 60a. The illustrated user interface chart 60 tracks the CD4 level against viral load. Along the left-hand side of the Y-axis 61 the CD4 count is plotted. Along the right-hand side of the Y-axis 61 the viral load count is plotted. The lines 62 represent the CD4 test and the viral load test as would be understood by those having skill in the art. Drug therapy for a time period is indicated within the area of the chart user interface 60 indicated as 63. Time is plotted along the X-axis 64, as illustrated.

Figure 6A:
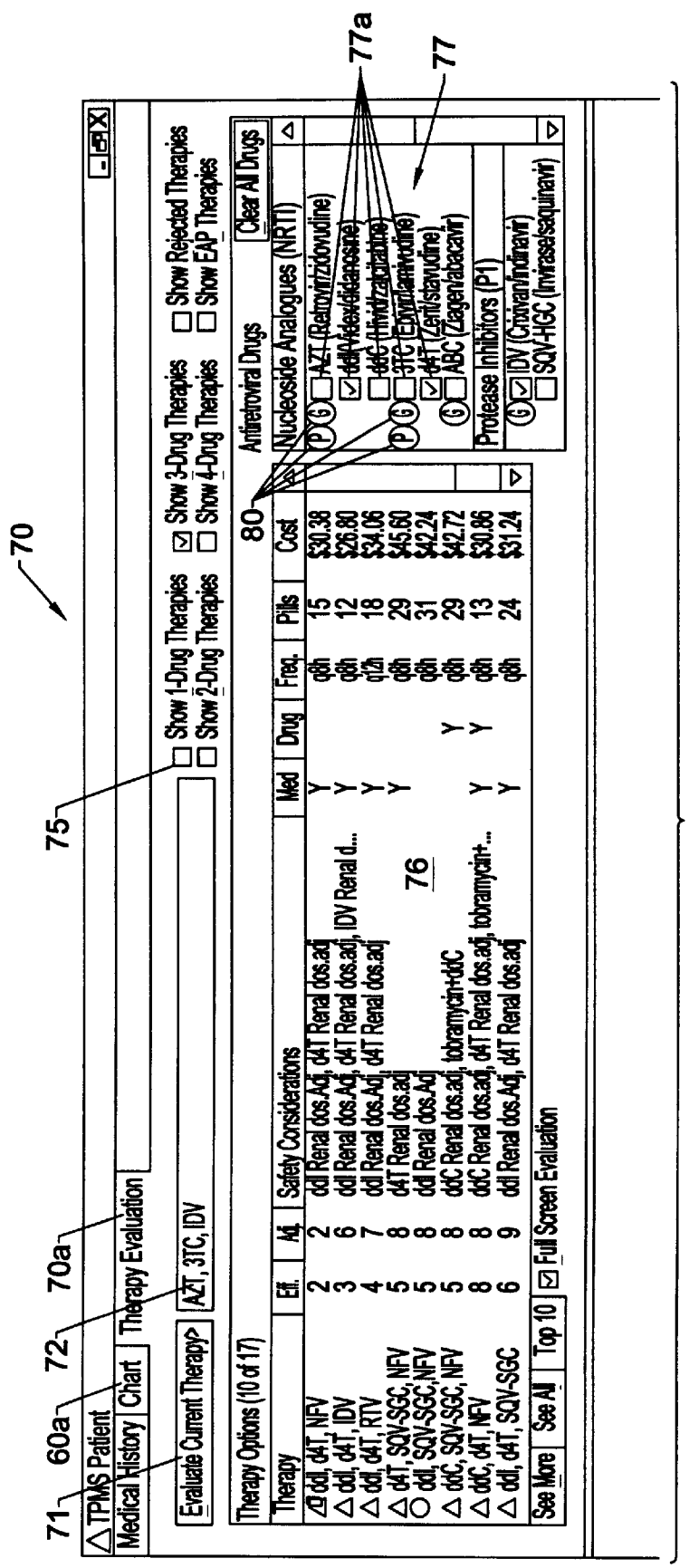
FIG. 6 illustrates a therapy evaluation user interface that facilitates evaluation of various therapeutic treatment regimen options with respect to relative efficacy, individualized adjusted relative efficacy, dosage, frequency, cost, medical complications and drug interactions according to the present invention.
Figure 6B:
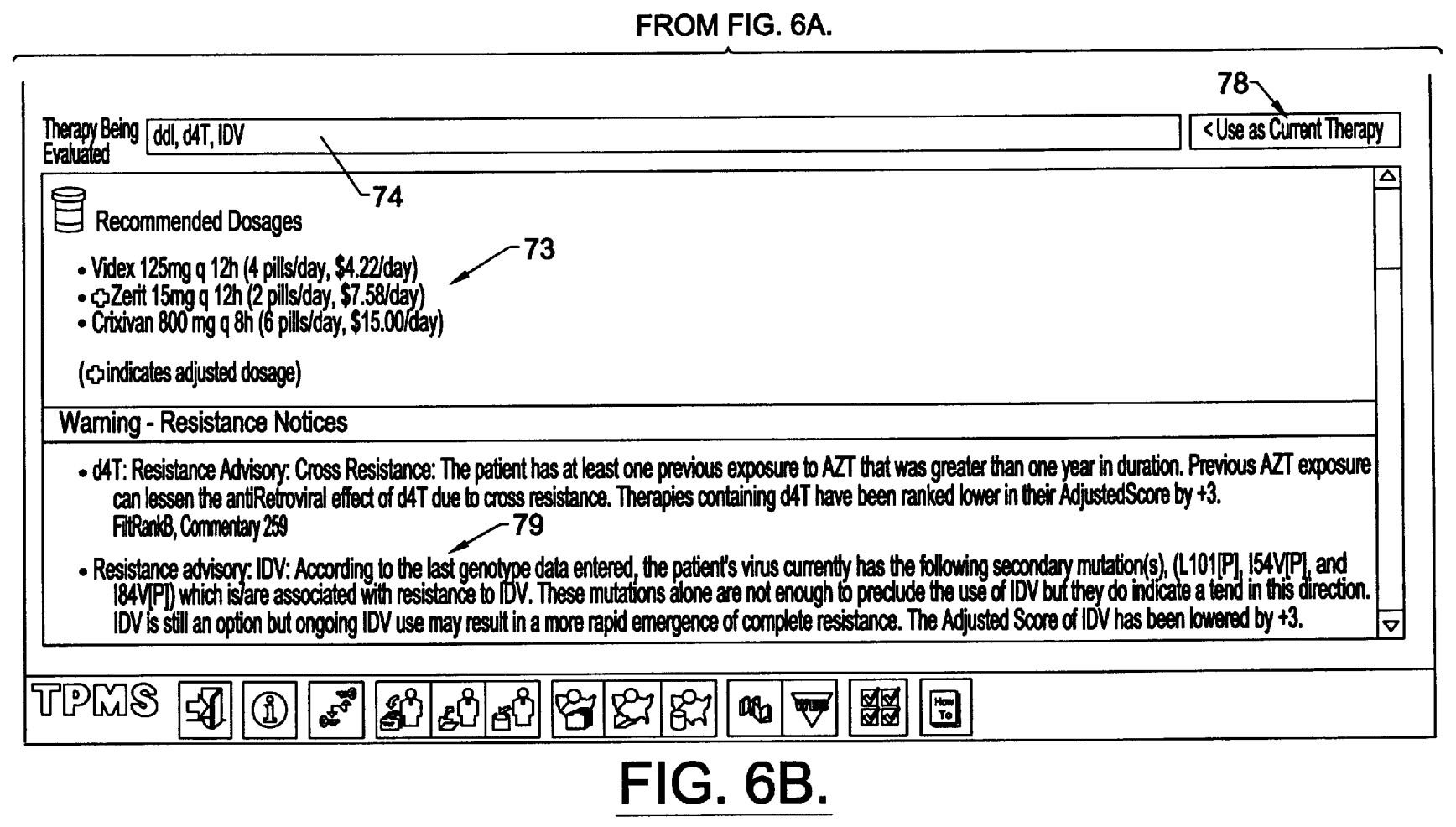

In FIG. 6, a therapy evaluation user interface 70 that facilitates evaluation of various therapy options with respect to relative efficacy, dosage, frequency, cost, medical complications and drug interactions is illustrated. The therapy evaluation user interface 70 can be displayed by activating the "Therapy Evaluation" tab 70a. Important elements in the illustrated therapy evaluation user interface 70 include an "Evaluate Current Therapy" button 71 for initiating an evaluation of a current therapy and a "Current Therapy" field 72 that lists a patient's current therapy. Detailed information about a patient's therapy is displayed in the therapy details box 73. A therapy displayed within box 73 is identified in box 74.

Multiple check boxes 75 are provided that allow a user to control how information is displayed within the therapy evaluation user interface 70. Within the therapy list box 76, a list of available therapies for a patient can be displayed. In the illustrated embodiment the drugs are listed in standard abbreviated form. Other information displayed with each drug may include that listed below in Table 5.

TABLE 5

| | |
|---|---|
| Efficacy Rating | Lists the therapy according to expected effectiveness only, regardless of patient specific considerations (1 is most effective). |
| Adjusted Score | This number uses the Efficacy Rating as a base and then the system adjusts it up or down based on patient specific conditions (1 is most effective). |
| Safety Considerations | A brief two or three word summary of the alerts associated with the therapy. |
| Frequency | Lists the dosage frequency (q12h, q24h, etc.). |
| Pills | Lists the total number of pills required per day for the complete regimen. |
| Cost | Lists the total cost of the regimen per day. |
| Medical Alert | Displays a Y if there is one or more Yellow Medical Alerts and an R if there is one or more Red Medical Alerts associated with the therapy. |
| Drug Interaction | Displays a Y if there is one or more Yellow Drug Interaction Alerts and an R if there is one or more Red Drug Interaction Alerts associated with the therapy. |

A list of available antiretroviral drugs is displayed within box 77. A user desiring to evaluate a particular combination of drugs can click the appropriate check boxes 77a to review information in the therapy details box 73. A "Use as Current Therapy" button 78 allows a user to apply a particular therapy to a patient. Various hyperlinks 79 within the therapy details box 73 allow a user to display specific information about a therapy evaluation. For example, a user can be allowed to view a rule which is associated with the displayed text.

Resistance evaluation alerts 80 can be provided adjacent each available antiretroviral drug displayed within box 77. For example, a blue "G" icon can be used to indicate that a patient's last genotype test contains mutations which are known to be associated with full or partial resistance to the antiretroviral drug. A red "P" icon can be used to indicate that a patient's last phenotype test demonstrates resistance to the antiretroviral drug.

Within the therapy list box 76, various symbols (described in FIG. 7) can be utilized to provide information about a drug therapy option. These symbols provide an instant graphical warning level for each therapy option. Some symbols, such as a red exclamation point, indicate that there is critical, possibly life threatening information in the therapy details box 73 for that therapy which must be read in order for that therapy to be properly utilized.

Figure 8:
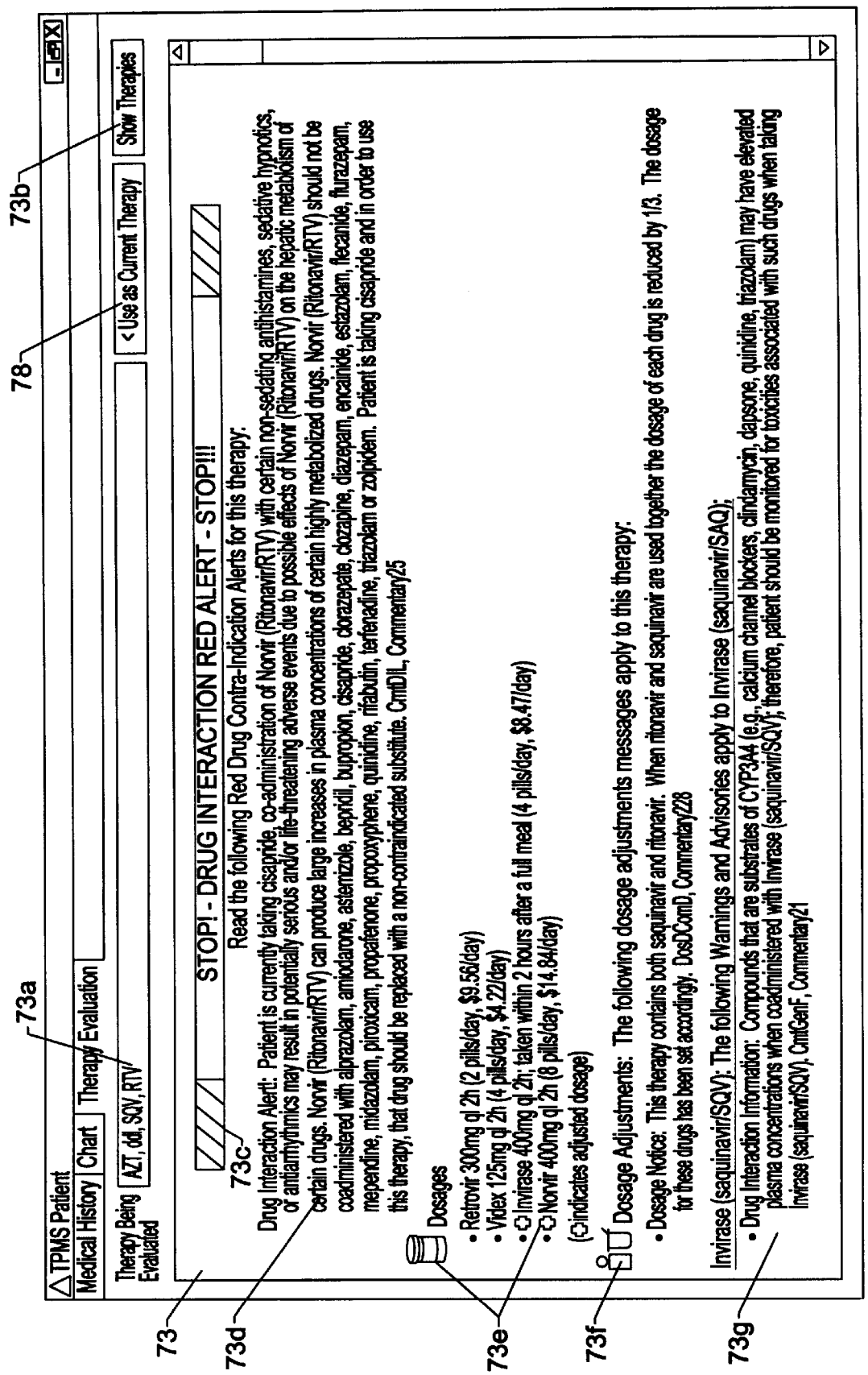
FIG. 8 illustrates the therapy details box of FIG. 6 in "full screen" mode.

When a drug therapy from the therapy list box 76 is selected by a user for evaluation, the therapy details box 73 of FIG. 6 can be displayed in "full screen" mode as illustrated in FIG. 8. Important elements in the illustrated therapy details box 73 include an identification box 73a for identifying the therapy being evaluated; a "Use as Current Therapy" button 78 that allows a user to apply a particular therapy to a patient; and a "Show Therapies" button 73b that returns the therapy details box 73 back to half-screen size as illustrated in FIG. 6. In addition, various hyperlinks may be embedded within text displayed within the therapy details box 73 that can be activated by a user to display various types of information. Eye catching alert banner(s) 73c and text 73d can be displayed at the top of the therapy details box 73 as illustrated. Dosages 73e of each drug, along with special administration instructions, can be displayed within the therapy details box 73 as illustrated. Dosage adjustment information 73f and various warnings and advisories 73g can also be displayed within the therapy details box 73 as illustrated.

According to a preferred embodiment of the present invention, therapeutic treatment regimens are not displayed to a user if an invalid drug is selected for treatment of a patient.

Physicians Desk Reference®

According to a preferred embodiment of the present invention, the Physicians Desk Reference® (PDR®) 28, which is a known drug reference source, is fully integrated with the system 20 of FIG. 2. Users can access the PDR® drug abstracts for antiretroviral drugs listed in the therapy list box 76 of the therapy evaluation user interface 70 of FIG. 6. In addition, users can access the PDR® on-line Web database to obtain additional information about a specific drug or to research a substitute for a contraindicated drug. When a user selects a drug within the therapy list box 76 of the therapy evaluation user interface 70, a web browser preferably is launched and the PDR® on-line Web database is accessed. Information can also be extracted from the PDR® on-line Web database to provide drug selection lists for non-antiretroviral drugs that a patient may be taking and to define relationships between brand name and generic drugs.

As illustrated in FIG. 9, a PDR® pop-up menu 90 may be provided that can be activated from within the therapy list box 76 of the therapy evaluation user interface 70 of FIG. 6. From the PDR® pop-up menu 90 a user can access various information from the PDR® including, but not limited to, drug abstracts, and generic components contained within a brand name drug.

The following non-limiting examples illustrate various aspects of the present invention. These examples are provided for illustrative purposes only, and are not intended to be limiting of the invention.

EXAMPLE 1

Figure 10A:
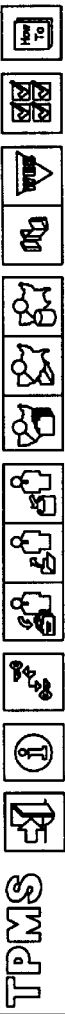
FIGS. 10A–10D illustrate various functions of the present invention as described in Example 1.

Example 1 will be explained with reference to FIGS. 10A–10D. Referring to FIG. 10A, a medical history user interface 50 containing evaluated data for patient "demo1" is illustrated. The group heading "Hemoglobin" 54*a* has changed colors to indicate to a user that the patient has an abnormally low hemoglobin value from a previous (historical) blood sampling. When the therapy evaluation tab 70*a* is activated to display the therapy evaluation user interface 70 (FIG. 10B) the associated medical condition warning of a history of anemia and the caution notification if using drugs known to be associated with hematopoetic toxicity is triggered as illustrated in the therapy details box 73 of FIG. 10B.

In addition, the group heading "Renal Function" 54*b* in FIG. 10*a* has changed colors to warn a user of potential renal dysfunction and is also indicated by the low estimated creatinine clearance rate in field F1 (which the system calculates using a mathematical formula taking patient age, sex, weight, and serum creatinine values—all of which are fields of the "Medical History" user interface 50). This information is pointed out to the user and is used if dosage adjustments are required for drugs that are known to be affected (cleared) by renal function.

Current and the next most recent $CD4^+$ cell count and viral load are displayed (F2, medical history user interface 50). This information is also used to determine when to start or change therapy and to evaluate the initial antiviral efficacy of a newly administered antiviral regimen.

Current and historical values for all fields in the medical history user interface 50 (FIG. 10A) can be viewed by pressing the "H" button beside fields that have this button.

Figure 10B:
Figure 10C:
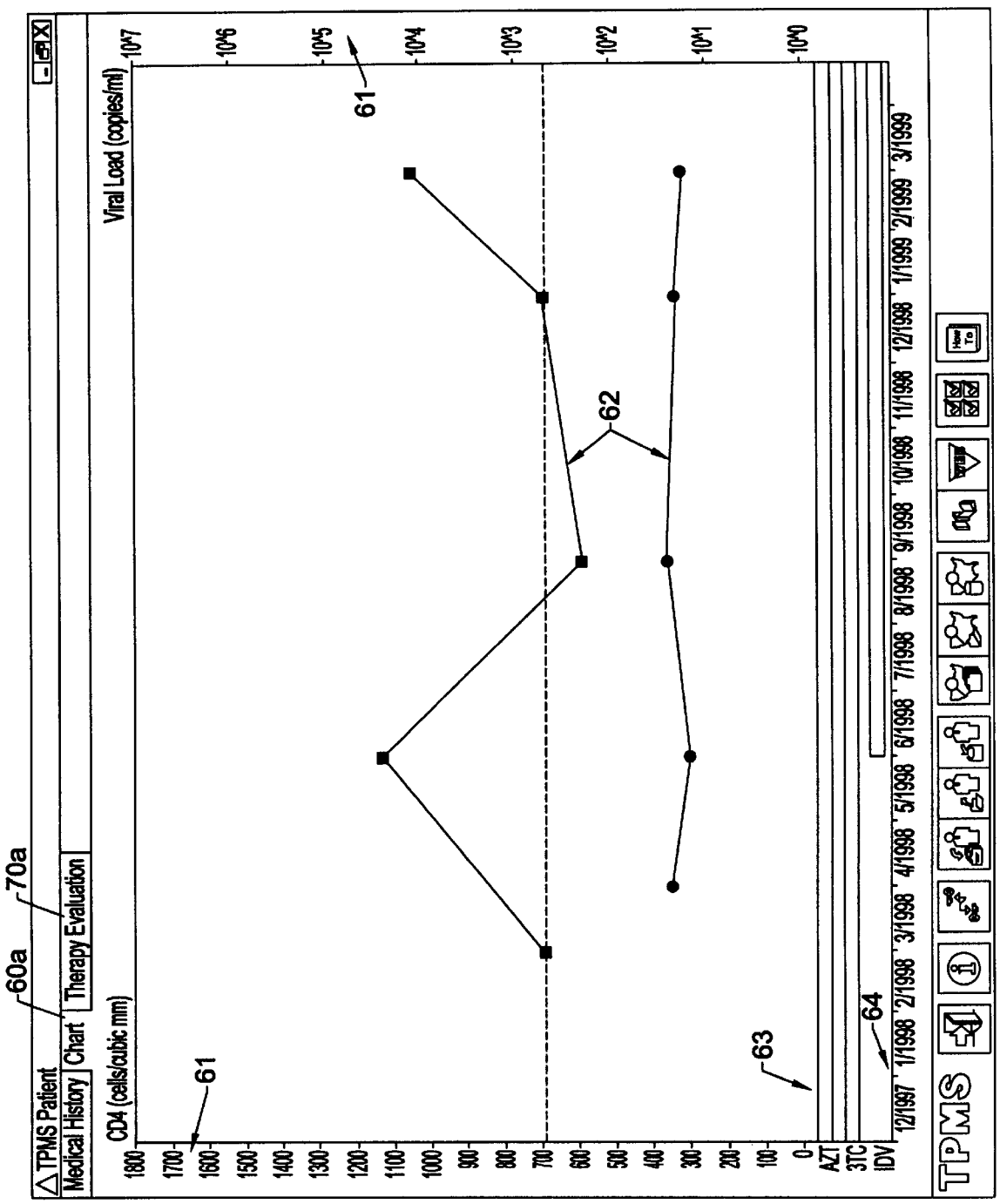

In FIG. 10C, the "Chart" user interface 60 has been activated. HIV RNA (viral load) is plotted on a log scale, the CD4 count is plotted on a linear scale, and the drug treatments are shown as Gantt bars on the horizontal date scale at the bottom of the chart user interface 60.

Figure 10D:
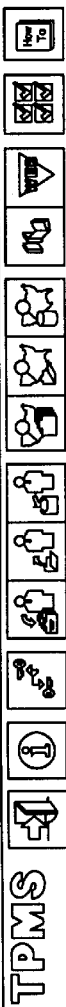

In FIG. 10D, the "Change Therapy Recommendation" message box MB1 pops up when the "Therapy Evaluation" tab 70*a* is selected. This box represents the processing of the data from the "Medical History" tab and the knowledge base output, including objective rules derived from published treatment guidelines, indicating that initiation of therapy, or a change of therapy in this case, may be called for if the other variable(s) indicated in the message have been addressed.

The list of available therapies and associated ranking order may be shown within the therapy details box 73 of FIG. 10B. This represents the output of the knowledge base for therapy selection. Included with the list of therapies can be any of the following: safety advisories (dosage adjustment, drug interaction, etc.) with a yellow triangle or red exclamation warning symbols; number of pills; daily cost of all three drugs; dosing regimen (q 8h, q 12 h, etc.); and dosages for all drugs in a regimen (including dosage adjustments if necessary) and pertinent information specific to the patient is listed in the dialog box.

EXAMPLE 2

Figure 11A:
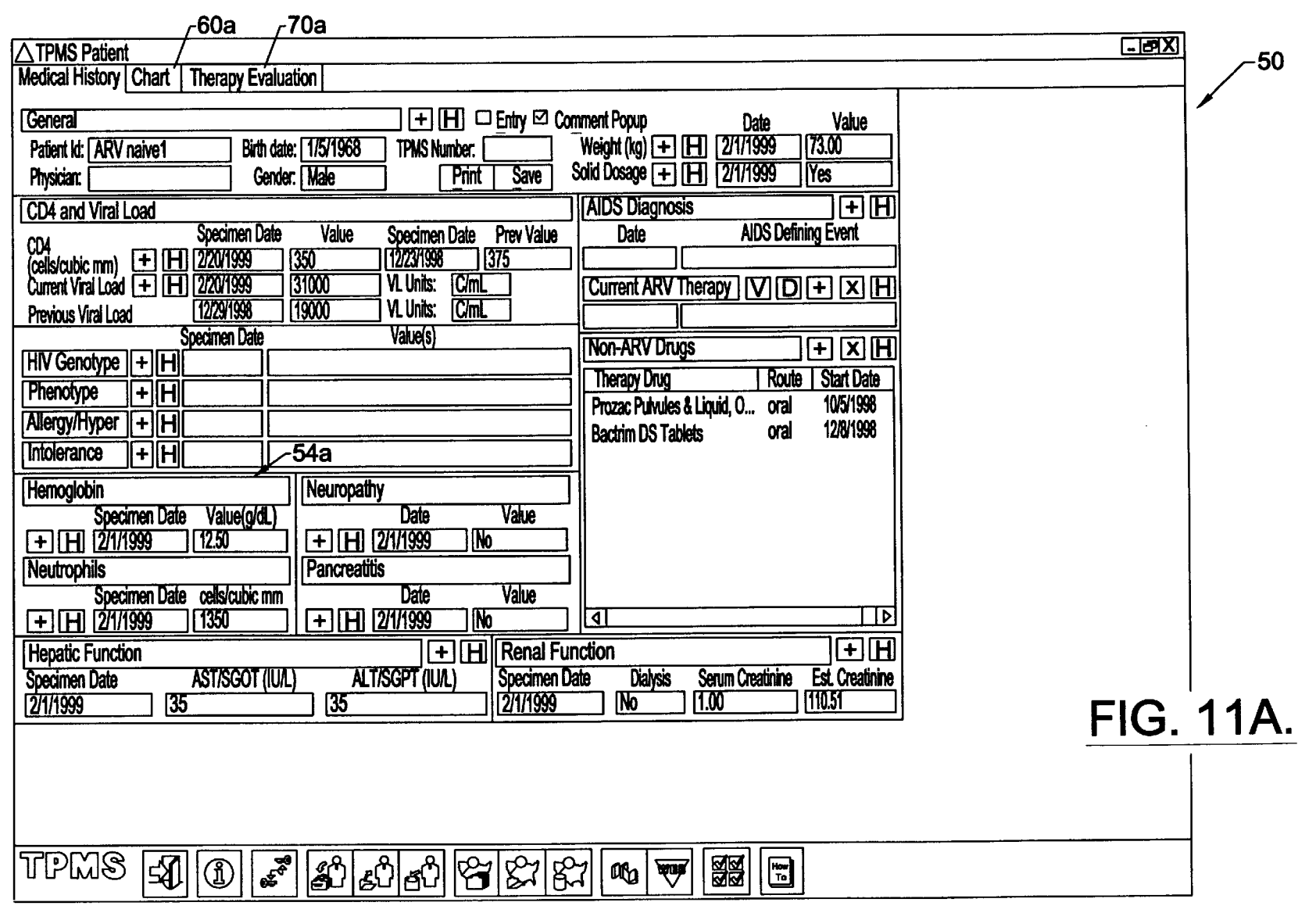
Figure 11B:
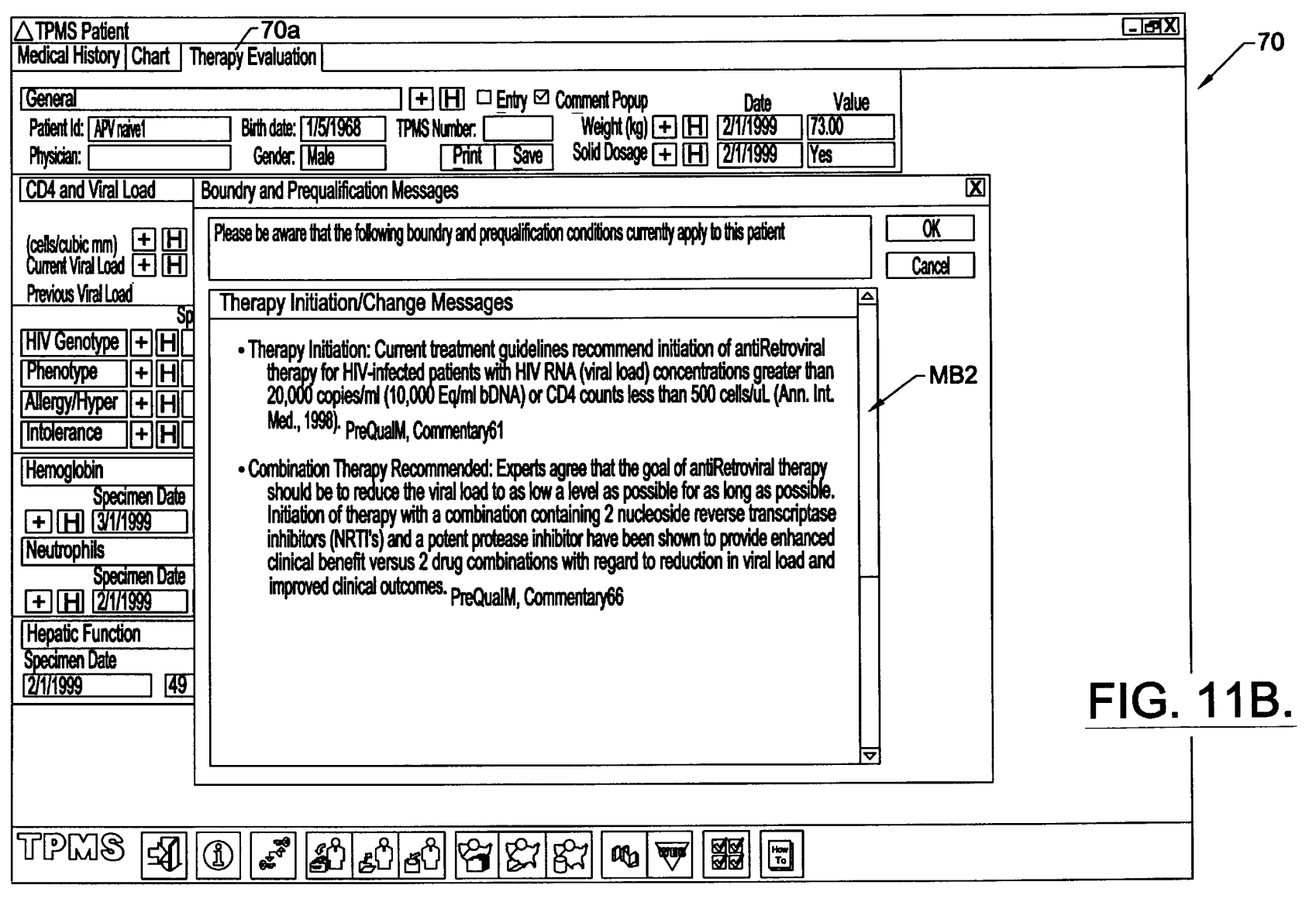
Figure 11C:
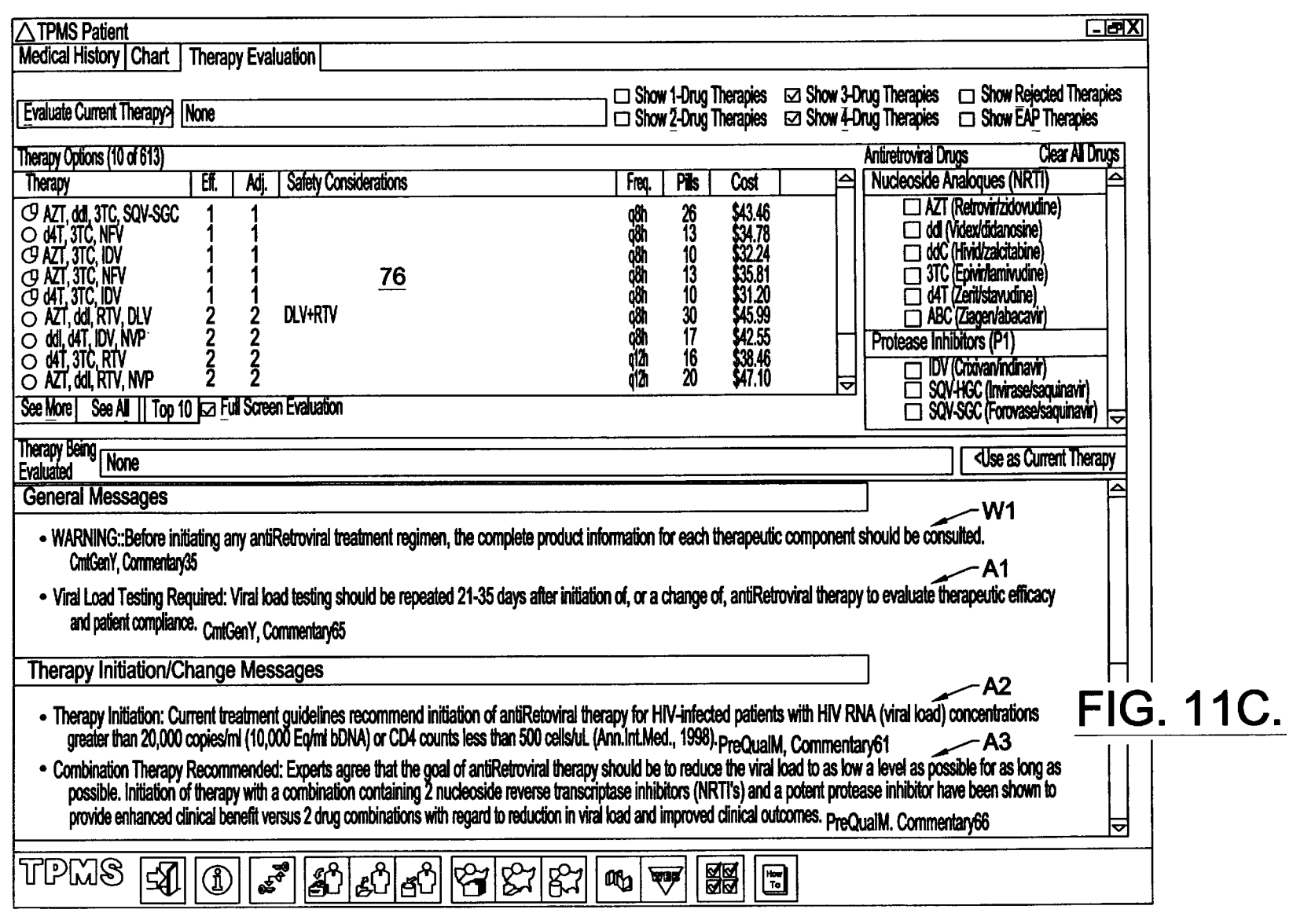
Figure 11E:

Example 2 will be explained with reference to FIGS. 11A–11E, and relates to patient file "ARV naivel" which is an example of an HIV-infected patient who has not been treated with anti-HIV drugs previously. In FIG. 11A, a medical history user interface 50 containing evaluated data for patient "ARV naive1" is illustrated. In FIG. 11B, when the "Therapy Evaluation" tab 70*a* is activated to display the therapy evaluation user interface 70, a "Boundary and Prequalification Messages" message box MB2 pops up indicating that according to the current, published, HIV treatment guidelines, the patient should be initiated on antiviral therapy and that the current guidelines recommend combinational therapy.

In FIG. 11C, the therapy evaluation user interface 70 has been activated and demonstrates features/functions associated with therapy evaluation including a general warning W1 and advisories A1, A2, and A3 for the patient related to treatment of the disease (e.g., whether therapy should be initiated or changed) or related to a specific therapy selected from the list box which is being evaluated by the user.

FIG. 11D illustrates various information that is displayable by clicking on an individual therapy in the therapy list box 76 of FIG. 11C. Information displayed includes dosages of all drugs with general and patient-specific warnings and advisories.

The features available by right clicking on any therapy listed in the therapy list box 76 of FIG. 11C are illustrated in FIG. 11E and include: linking to an electronic PDR® to show drug package insert information or perform drug search information; showing or hiding columns of information displayed within the therapy list box; linking to a publication or abstract associated with a therapy that has a "book" icon associated therewith; and various printing functions.

EXAMPLE 3

Figure 12A:
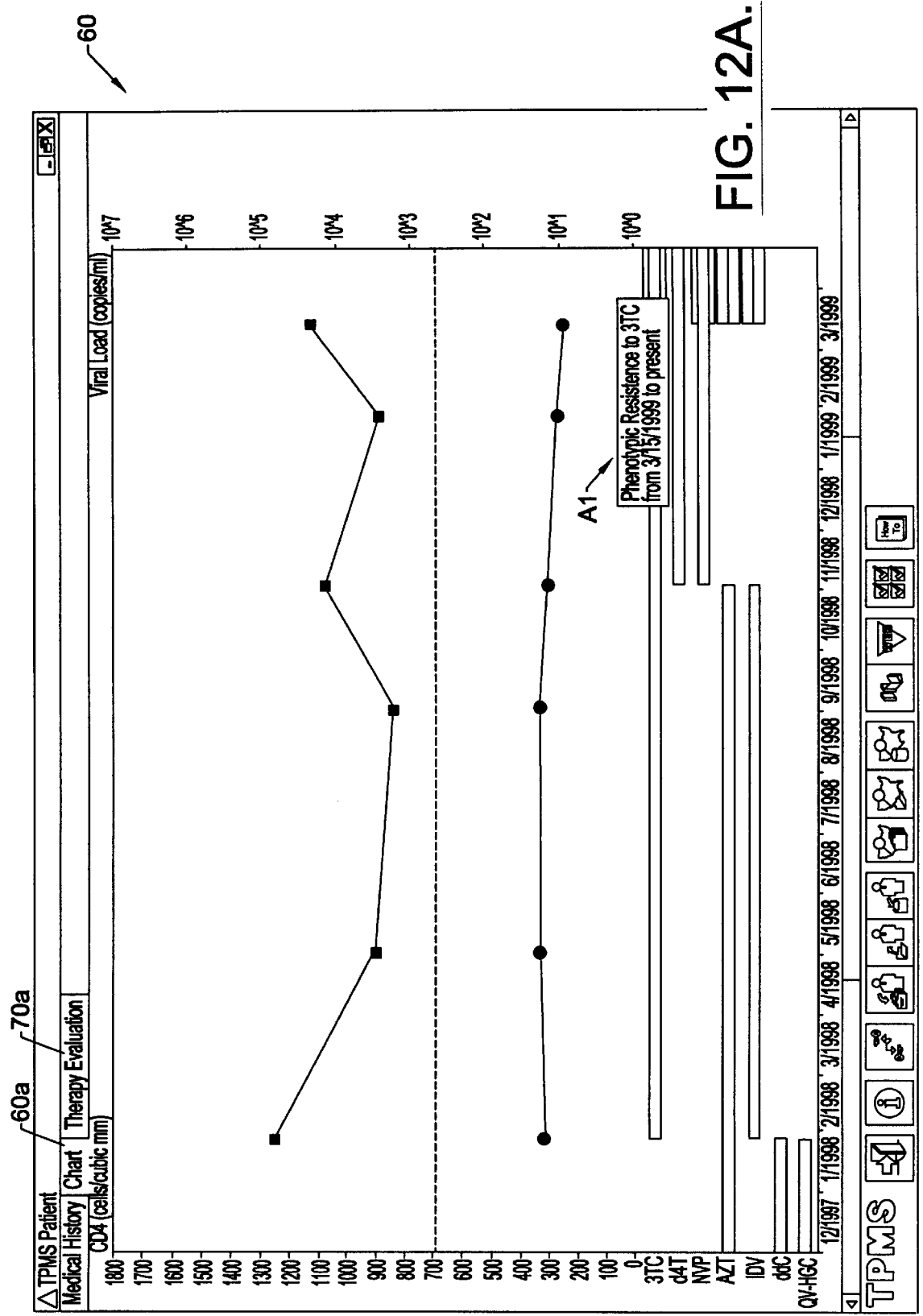
Figure 12B:
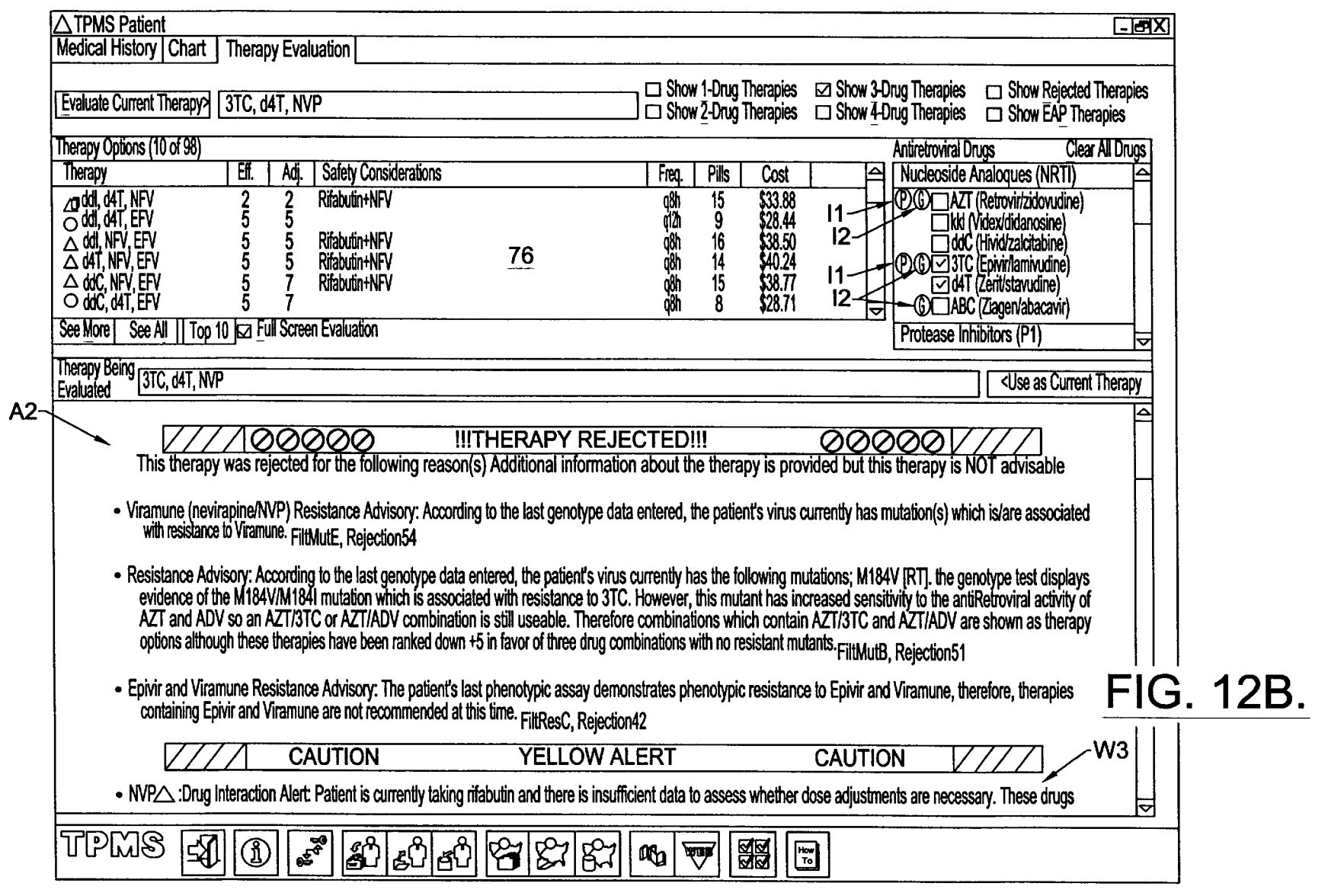
Figure 12C:

Example 3 will be explained with reference to FIGS. 12A–12C, and relates to patient file "Features1" which illustrates some important functions/features that a system according to the present invention can provide for highly drug experienced patients who may have developed resistance associated with the use of several antiviral drugs. Features, including functions attributed to the new resistance and historical therapy rules are illustrated and includes:

1) Potential drug resistance advisories (A1, FIG. 12A) when the chart tab 60a is activated, or (A2, FIG. 12B) when the therapy evaluation tab 70a is activated;
2) The heads up "P" and "G" indicators (I1 and I2, FIG. 12B) to remind of phenotypic or genotypic resistance associated with certain anti-HIV compounds as demonstrated for this patient (including indication of expected/anticipated genotypic resistance, as a result of cross-resistance, to a drug that a patient may not be taking currently or has not previously taken);
3) The drug interaction warning system (indicated by warning W3, FIG. 12C). Warning W3 is for the interaction between Nevirapine and rifabutin (which was selected from the list of non-antiretroviral drugs available as part of the medical history user interface 50). The drug interaction warning message may be viewed from the medical history user interface 50 by "right-clicking" the non-ARV title bar 54C, which has turned yellow indicating the presence of an ARV-nonARV drug interaction. This information is also prominently displayed for the user on the therapy evaluation user interface 70 as a text message (W3, FIG. 12B) as well as in the "Safety Considerations" section of the drug list box (76, FIG. 12B); and
4) The chart user interface 60 (FIG. 12A) illustrates the viral load, CD4, drug therapies, and associated drug resistance in graphic form for the user to evaluate.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for guiding the selection of a therapeutic treatment regimen for a patient with a known disease or medical condition, said method comprising:
    (a) providing patient information to a computing device comprising:
        a first knowledge base comprising a plurality of different therapeutic treatment regimens for said disease or medical condition;
        a second knowledge base comprising a plurality of expert rules for evaluating and selecting a therapeutic treatment regimen for said disease or medical condition;
        a third knowledge base comprising advisory information useful for the treatment of a patient with different constituents of said different therapeutic treatment regimens; and
    (b) generating in said computing device a ranked listing of available therapeutic treatment regimens for said patient; and
    (c) generating in said computing device advisory information for one or more therapeutic treatment regimens in said ranked listing based on said patient information and said expert rules.

2. A method according to claim 1, further comprising the steps of:
    (d) entering a user-defined therapeutic treatment regimen for said disease or medical condition that is not included in said first knowledge base;
    (e) generating in said computing device advisory information for said user-defined combination therapeutic treatment regimen.

3. A method according to claim 1, further comprising the steps of:
    (f) entering a non-recommended therapeutic treatment regimen for said disease or medical condition that is included in said first knowledge base but not recommended from said ranked listing; and
    (g) generating in said computing device advisory information for said non-recommended therapeutic treatment regimen, said advisory information including at least one reason for non-recommendation of said therapeutic treatment regimen.

4. A method according to claim 1, said patient information comprising gender, age, weight, CD4 information, viral load information, HIV genotype and phenotype information, hemoglobin information, neuropathy information, neutrophil information, pancreatitis, hepatic function, renal function, drug allergy and intolerance information.

5. A method according to claim 1, said patient information including prior therapeutic treatment regimen information.

6. A method according to claim 1, wherein said patient information includes prior patient information stored in said computing device.

7. A method according to claim 1, said advisory information including:
    warnings to take the patient off a contraindicated drug before initiating a corresponding therapeutic treatment regimen; and
    information clinically useful to implement a corresponding therapeutic treatment regimen.

8. A method according to claim 1, wherein said computing device comprises a fourth knowledge base comprising patient therapeutic treatment regimen history, said advisory information including previous therapeutic treatment regimen information extracted from said fourth knowledge base.

9. A method according to claim 7, wherein said known disease or medical condition is HIV-1 infection, said therapeutic treatment regimen includes antiretroviral drugs, and said therapeutic treatment regimen includes contraindicated or potentially adversely interacting non-antiretroviral drugs.

10. A method according to claim 7, wherein said therapeutic treatment regimen includes a protease inhibitor, and said contraindicated drug is terfenadine.

11. A method according to claim 7, wherein said therapeutic treatment regimen includes indinavir and said contraindicated drug is cisapride.

12. A method according to claim 1, wherein said known disease or medical condition is one where multiple prophylactic or therapeutic treatment regimens are available to be used singly or in combination in the treatment of said disease.

13. A method according to claim 1, wherein said known disease or medical condition is a cardiovascular disease.

14. A method according to claim 1, wherein said known disease or medical condition is a pulmonary disease.

15. A method according to claim 1, wherein said known disease or medical condition is a neurologic disease.

16. A method according to claim 1, wherein said known disease or medical condition is cancer.

17. A method according to claim 1, wherein said known disease or medical condition is a urinary tract infection.

18. A method according to claim 1, wherein said known disease or medical condition is hepatitis.

19. A method according to claim 1, wherein said known disease or medical condition is HIV-1 infection.

20. A method according to claim 1, wherein said first knowledge base comprises a plurality of different combination therapeutic treatment regimens.

21. A method according to claim 1, wherein drug dosage information is recommended and adjusted if necessary depending upon said patient information.

22. A method according to claim 1, further comprising the step of:
(d) accessing, via said computing device, information for one or more therapeutic treatment regimens from a drug reference source.

23. A system for guiding the selection of a therapeutic treatment regimen for a patient with a known disease or medical condition, said system comprising:
(a) a computing device comprising:
a first knowledge base comprising a plurality of different therapeutic treatment regimens for said disease or medical condition;
a second knowledge base comprising a plurality of expert rules for selecting a therapeutic treatment regimen for said disease or medical condition;
a third knowledge base comprising advisory information useful for the treatment of a patient with different constituents of said different therapeutic treatment regimens; and
(b) means for providing patient information to said computing device;
(c) means for generating in said computing device a ranked listing of therapeutic treatment regimens for said patient; and
(d) means for generating in said computing device advisory information for one or more therapeutic treatment regimens in said ranked listing based on said patient information and said expert rules.

24. A system according to claim 23, further comprising:
(e) means for entering a user-defined therapeutic treatment regimen for said disease or medical condition that is not generated or displayed via said first knowledge base;
(f) means for generating in said computing device advisory information for said user-defined combination therapeutic treatment regimen.

25. A system according to claim 23, further comprising:
(f) means for entering a non-recommended therapeutic treatment regimen for said disease or medical condition that is included in said first knowledge base but not recommended from said ranked listing; and
(g) means for generating in said computing device advisory information for said non-recommended therapeutic treatment regimen, said advisory information including at least one reason for non-recommendation of said therapeutic treatment regimen.

26. A system according to claim 23, said patient information comprising gender, age, weight, CD4 information, viral load information, HIV genotype and phenotype information, hemoglobin information, neuropathy information, neutrophil information, pancreatitis, hepatic function, renal function, drug allergy and intolerance information.

27. A system according to claim 23, said patient information including prior therapeutic treatment regimen information.

28. A system according to claim 23, wherein said patient information includes prior patient information stored in said computing device.

29. A system according to claim 23, said advisory information including:
warnings to take the patient off a contraindicated drug before initiating a corresponding therapeutic treatment regimen; and
information clinically useful to implement a corresponding therapeutic treatment regimen.

30. A system according to claim 23, wherein said computing device comprises a fourth knowledge base comprising patient therapeutic treatment regimen history, said advisory information including previous therapeutic treatment regimen information extracted from said fourth knowledge base.

31. A system according to claim 29, wherein said known disease or medical condition is HIV-1 infection, said therapeutic treatment regimen includes antiretroviral drugs, and said therapeutic treatment regimen includes contraindicated or potentially adversely interacting non-antiretroviral drugs.

32. A system according to claim 29, wherein said therapeutic treatment regimen includes a protease inhibitor, and said contraindicated drug is terfenadine.

33. A system according to claim 29, wherein said therapeutic treatment regimen includes indinavir and said contraindicated drug is cisapride.

34. A system according to claim 23, wherein said known disease or medical condition is one where multiple prophylactic therapeutic treatment regimens are available to be used singly or in combination in the treatment of said disease or medical condition.

35. A system according to claim 23, wherein said known disease or medical condition is a cardiovascular disease.

36. A system according to claim 23, wherein said known disease or medical condition is a pulmonary disease.

37. A system according to claim 23, wherein said known disease or medical condition is a neurologic disease.

38. A system according to claim 23, wherein said known disease or medical condition is cancer.

39. A system according to claim 23, wherein said known disease or medical condition is a urinary tract infection.

40. A system according to claim 23, wherein said known disease or medical condition is hepatitis.

41. A system according to claim 23, wherein said known disease or medical condition is HIV-1 infection.

42. A system according to claim 23, wherein said first knowledge base comprises a plurality of different combination therapeutic treatment regimens.

43. A system according to claim 23, wherein drug dosage information is recommended and adjusted if necessary depending upon said patient information.

44. A system according to claim 23, further comprising:
(e) means for accessing, via said computing device, information for one or more therapeutic treatment regimens from a standard drug reference source.

45. A computer program product for guiding the selection of a therapeutic treatment regimen for a patient with a known disease or medical condition, said computer program product comprising a computer usable storage medium having computer readable program code means embodied in the medium, the computer readable program code means comprising:

(a) computer readable program code means for generating:
- a first knowledge base comprising a plurality of different therapeutic treatment regimens for said disease or medical condition;
- a second knowledge base comprising a plurality of expert rules for selecting a therapeutic treatment regimen for said disease or medical condition;
- a third knowledge base comprising advisory information useful for the treatment of a patient with different constituents of said different therapeutic treatment regimens; and (b) computer readable program code means for providing patient information;

(c) computer readable program code means for generating a ranked listing of available therapeutic treatment regimens for said patient; and (d) computer readable program code means for generating advisory information for one or more therapeutic treatment regimens in said ranked listing based on said patient information and said expert rules.

46. A computer program product according to claim 45, further comprising:
(e) computer readable program code means for entering a user-defined therapeutic treatment regimen for said disease or medical condition that is not generated or displayed via said first knowledge base;
(f) computer readable program code means for generating advisory information for said user-defined combination therapeutic treatment regimen.

47. A computer program product according to claim 46, further comprising:
(g) computer readable program code means for entering a non-recommended therapeutic treatment regimen for said disease or medical condition that is included in said first knowledge base but not recommended from said ranked listing; and
(h) computer readable program code means for generating advisory information for said non-recommended therapeutic treatment regimen, said advisory information including at least one reason for non-recommendation of said therapeutic treatment regimen.

48. A computer program product according to claim 45, said patient information comprising gender, age, weight, CD4 information, viral load information, HIV genotype and phenotype information, hemoglobin information, neuropathy information, neutrophil information, pancreatitis, hepatic function, renal function, drug allergy and intolerance information.

49. A computer program product according to claim 45, said patient information including prior therapeutic treatment regimen information.

50. A computer program product according to claim 45, wherein said patient information includes prior patient information.

51. A computer program product according to claim 45, said advisory information including:
warnings to take the patient off a contraindicated drug before initiating a corresponding therapeutic treatment regimen; and
information clinically useful to implement a corresponding therapeutic treatment regimen.

52. A computer program product according to claim 45 wherein said computer readable program code means comprises computer readable program code means for generating a fourth knowledge base comprising patient therapeutic treatment regimen history, said advisory information including previous therapeutic treatment regimen information extracted from said fourth knowledge base.

53. A computer program product according to claim 51, wherein said known disease or medical condition is HIV-1 infection, said therapeutic treatment regimen includes antiretroviral drugs, and said therapeutic treatment regimen includes contraindicated or potentially adversely interacting non-antiretroviral drugs.

54. A computer program product according to claim 51, wherein said therapeutic treatment regimen includes a protease inhibitor, and said contraindicated drug is terfenadine.

55. A computer program product according to claim 51, wherein said therapeutic treatment regimen includes indinavir and said contraindicated drug is cisapride.

56. A computer program product according to claim 45, wherein said known disease or medical condition is one where multiple prophylactic therapeutic treatment regimens are available to be used singly or in combination in the treatment of said disease or medical condition.

57. A computer program product according to claim 45, wherein said known disease or medical condition is a cardiovascular disease.

58. A computer program product according to claim 45, wherein said known disease or medical condition is a pulmonary disease.

59. A computer program product according to claim 45, wherein said known disease or medical condition is a neurologic disease.

60. A computer program product according to claim 45, wherein said known disease or medical condition is cancer.

61. A computer program product according to claim 45, wherein said known disease or medical condition is a urinary tract infection.

62. A computer program product according to claim 45, wherein said known disease or medical condition is hepatitis.

63. A computer program product according to claim 45, wherein said known disease or medical condition is HIV-1 infection.

64. A computer program product according to claim 45, wherein said first knowledge base comprises a plurality of different combination therapeutic treatment regimens.

65. A computer program product according to claim 45, wherein drug dosage information is recommended and adjusted if necessary depending upon said patient information.

66. A computer program product according to claim 45, further comprising:
(e) computer readable program code means for accessing information for one or more therapeutic treatment regimens from a standard drug reference source.

* * * * *

US006081786C1

(12) EX PARTE REEXAMINATION CERTIFICATE (7058th)

United States Patent
Barry et al.

(10) Number: US 6,081,786 C1
(45) Certificate Issued: Sep. 15, 2009

(54) SYSTEMS, METHODS AND COMPUTER PROGRAM PRODUCTS FOR GUIDING THE SELECTION OF THERAPEUTIC TREATMENT REGIMENS

(75) Inventors: David W. Barry, Chapel Hill, NC (US); Carolyn S. Underwood, Cary, NC (US); Bruce J. McCreedy, Raleigh, NC (US); David D. Hadden, Durham, NC (US); Jason L. Lucas, West Chester, PA (US)

(73) Assignee: Advanced Biological Laboratories, SA, Luxembourg (LU)

Reexamination Request:
No. 90/010,313, Oct. 10, 2008
No. 90/009,204, Oct. 14, 2008

Reexamination Certificate for:
Patent No.: 6,081,786
Issued: Jun. 27, 2000
Appl. No.: 09/283,702
Filed: Apr. 1, 1999

Related U.S. Application Data
(60) Provisional application No. 60/080,629, filed on Apr. 3, 1998.

(51) Int. Cl.
*G06F 19/00* (2006.01)

(52) U.S. Cl. .................... 705/3; 705/2; 706/45; 706/46; 706/47; 706/924

(58) Field of Classification Search ........................ None
See application file for complete search history.

(56) References Cited

PUBLICATIONS

Shortliffe, E.H., "*Mycin: A Rule–Based Computer Program for Advising Physicians Regarding Antimicrobial Therapy Selection,*" (Ph.D. thesis, Stanford University) (on file with Mathematical and Computer Sciences Library, Stanford University), Stanford Artificial Intelligence Laboratory Memo AIM–251, Computer Science Department Report No. STAN–CS–74–465, National Technical Information Service (NTIS) Technical Report No. AD–A001 373 (1974).

Kulikowski, C.A. and Weiss, S.M., "Representation of Expert Knowledge for Consultation: The Casnet and Expert Projects," in *Artificial Intelligence in Medicine*, pp. 21–55, (Peter Szolovits ed., Westview Press, Boulder, CO) (1982).

Miller, P.L. and Black, H.R., "Medical Plan–Analysis by Computer: Critiquing Pharmacologic Management of Essential Hypertension," *Computers and Biomedical Research* 17:38–54 (1984).

Siepman, J.P. and Bachman, J.W., "HTN–APT: Computer Aid in Hypertension Management," *Journal of Family Practice* 24:313–316 (1987).

Evans, R.S., et al., "Development of an Automated Antibiotic Consultant," *M.D. Computing: Computers in Medical Practice* 10:17–22 (1993).

Pazzani, M., et al., "CTSHIV: A Knowledge–Based System For the Management of HIV–infected Patients," in *Intelligent Information Systems*, pp. 7–13 (Hojjat Adeli ed., IEEE Computer Society, Los Alamitos, CA) (1997).

(Continued)

*Primary Examiner*—Deandra M Hughes

(57) ABSTRACT

Systems, methods and computer program products for guiding selection of a therapeutic treatment regimen for a known disease such as HIV infection are disclosed. The method comprises (a) providing patient information to a computing device (the computer device comprising: a first knowledge base comprising a plurality of different therapeutic treatment regimens for the disease; a second knowledge base comprising a plurality of expert rules for selecting a therapeutic treatment regimen for the disease; and a third knowledge base comprising advisory information useful for the treatment of a patient with different constituents of the different therapeutic treatment regimens; and (b) generating in the computing device a listing (preferably a ranked listing) of therapeutic treatment regimens for the patient; and (c) generating in the computing device advisory information for one or more treatment regimens in the listing based on the patient information and the expert rules.

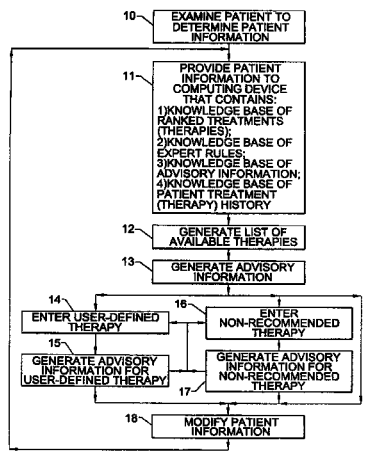

OTHER PUBLICATIONS

Hickman, D.H., et al., "The Treatment Advice of a Computer-Based Cancer Chemotherapy Protocol Advisor," *Annals of Internal Medicine* 103:928–936 (1985).

Langlotz, C.P., et al., "A Therapy Planning Architecture That Combines Decision Theory and Artificial Intelligence Techniques," *Computers and Biomedical Research* 20:279–303 (1987).

Evans, R.S., et al., "A Decision Support Tool for Antibiotic Therapy," *1995 Proceedings of the Annual Symposium on Computer Applications in Medical Care*, pp. 651–655 (1995).

Degoulet, P., et al., "Computer-assisted Techniques for Evaluation and Treatment of Hypertensive Patients," *American Journal of Hypertension* 3:156–163 (1990).

Perry, C.A., "Knowledge bases in medicine: a review" *Bulletin of the Medical Library Association* 78:271–282 (1990).

Nienow, J.R., Spach, D.H., Hooton, T.M, and Collier, A.C., "Antiretroviral Therapy," in *The HIV Manual: A Guide to Diagnosis and Treatment*, pp. 60–88 (David H. Spach & Thomas M. Hooton eds., Oxford University Press, New York) (1996).

Shafer, R.W. and Merigan, T.C., "Editorial: New Virologic Tools for the Design and Analysis of Clinical Trials," *Journal of Infectious Diseases*, 171:1325–1328 (1995).

Bartlett, J.G., *Medical Management of HIV Infection* (available as Internet pages archived on Jun. 1, 1997): • http://web.archive.org/web/19970601005020/www.hopkins-aids.edu/jhas_htmlcode/jhas_book/jhas_book.html • http://web.archive.org/web/19970601005936/www.hopkins-aids.edu/jhas_htmlcode/jhas_book/D.MedMgt.Ch01.FM.html • http://web.archive.org/web/19970601005953/www.hopkins-aids.edu/jhas_htmlcode/jhas_book/D.MedMgt.Ch02.FM.html • http://web.archive.org/web/19970601010004/www.hopkins-aids.edu/jhas_htmlcode/jhas_book/D.MedMgt.Ch03.FM.html • http://web.archive.org/web/19970601010016/www.hopkins-aids.edu/jhas_htmlcode/jhas_book/D.MedMgt.Ch04.FM.html • http://web.archive.org/web/19970601010035/www.hopkins-aids.edu/jhas_htmlcode/jhas_book/D.MedMgt.Ch05.FM.html.

• http://web.archive.org/web/19970601010059/www.hopkins-aids.edu/jhas_htmlcode/jhas_book/D.MedMgt.Ch06.FM.html • http://web.archive.org/web/19970601010059/www.hopkins-aids.edu/jhas_htmlcode/jhas_book/D.MedMgt.Ch07.FM.html.

Bartlett, J.G., *Medical Management of HIV Management of HIV Infection* (Port City Press, Baltimore) (1997).

Rule-Based Expert Systems: The Mycin Experiments of the Stanford Heuristic Programming Project (Bruce G. Buchanan & Edward H. Shortliffe eds., Addison-Wesley Publishing) (1984).

James P. Siepmann & John W. Bachman, *HTN-APT: computer aid in hypertension management*, J FAM PRACT. Mar. 1987, 24(3):313–6.

Michael Pazzani et al., *CTSHIV: A knowledge-based system for the management of HIV-infected patients*, 1997 Intelligent Information Systems, IIS '97 Proc. 7–13.

Perry L. Miller & Henry R. Black, *HT-Attending: Critiquing the Pharmacologic Management of Essential Hypertension*, 1983 IEEE The Seventh Annual Symposium on Computer Applications in Medical Care. 824–27.

Gilad J. Kuperman et al., *Help: A Dynamic Hospital Information System* (Helmuth F. Orthner ed., Spring-Verlag New York) (1991).

I. Vlahavas et al., *IDIS-KS: an intelligent drug information system as a knowledge server*. 1997 Stud Health Technol Inform. 43, Pt A:368–72.

*Public Health Service Guidelines for the Management of Health-Care Worker Exposures to HIV and Recommendations for Postexposure Prophylaxis*, Virginia Epidemiology Bulletin 98(3):1–8 (Elizabeth Barrett ed. Mar. 1998).

Homer Warner, Jr. et al., *New computer-based tools for empiric antibiotic decision support*. 1997 Proc Amia Annu Fall Symp. 1–5.

Y. K. Zhao et al., *Design and development of an expert system to assist diagnosis and treatment of chronic hepatitis using traditional Chinese medicine*. Med Inform (Lond.) Jan.–Mar. 19(1):37–45 (1994).

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–66 is confirmed.

* * * * *

EX PARTE REEXAMINATION CERTIFICATE (7457th)

United States Patent
Barry et al.

(10) Number: US 6,081,786 C2
(45) Certificate Issued: Apr. 13, 2010

(54) SYSTEMS, METHODS AND COMPUTER PROGRAM PRODUCTS FOR GUIDING THE SELECTION OF THERAPEUTIC TREATMENT REGIMENS

(75) Inventors: David W. Barry, Chapel Hill, NC (US); Carolyn S. Underwood, Cary, NC (US); Bruce J. McCreedy, Raleigh, NC (US); David D. Hadden, Durham, NC (US); Jason L. Lucas, West Chester, PA (US)

(73) Assignee: Advanced Biological Laboratories, SA, Luxembourg (LU)

Reexamination Request:
No. 90/010,600, Jul. 31, 2009

Reexamination Certificate for:
Patent No.: 6,081,786
Issued: Sep. 15, 2009
Appl. No.: 09/283,702
Filed: Apr. 1, 1999

Reexamination Certificate B1 6,081,786 issued Jun. 27, 2000

Related U.S. Application Data
(60) Provisional application No. 60/080,629, filed on Apr. 3, 1998.

(51) Int. Cl.
*G06F 19/00* (2006.01)

(52) U.S. Cl. .................... 705/3; 705/2; 706/45; 706/46; 706/47; 706/924

(58) Field of Classification Search .................... 705/3
See application file for complete search history.

(56) References Cited

PUBLICATIONS

Francis Lau, "A clinical decision support system prototype for cardiovascular intensive care," Int'l J. of Clinical Monitoring and Computing, 11:157–69 (1994).

Ong Lean Suan, "Computer–Aided Diagnosis and Treatment of Malaria: The IMEX System," Comp. Biol. Med. No. 5, 361–72 (1990).

Nienow, et al., "Antiretroviral Therapy, in The HIV Manual; A Guide to Diagnosis and Treatment," p. 60–88 (D.H. Spach and T.M. Hooten eds., Oxford University Press (1996).

Claudia A. Perry, "Knowledge bases in medicine: a review," Bulletin of the Medical Library Association 78:271–82 (1990).

Piotr Windyga, et al., "Knowledge–based approach to the management of serious arrhythmia in the CCU," Med. & Biol. Eng'g & Computing, 29:254–60 (May 1991).

Gert Jan Van Heijst, et al., "Foundations for a methodology for medical KBS development," Knowledge Acquisition 6, 395–434 (1994).

"Rule–Based Expert Systems: The MYCIN Experiments of the Stanford Heuristic Programming Project" (Bruce Buchanan & Edward Shortliffe eds., Addison–Wesley Publishing (1984).

*Primary Examiner* — Deandra Hughes

(57) ABSTRACT

Systems, methods and computer program products for guiding selection of a therapeutic treatment regimen for a known disease such as HIV infection are disclosed. The method comprises (a) providing patient information to a computing device (the computer device comprising: a first knowledge base comprising a plurality of different therapeutic treatment regimens for the disease; a second knowledge base comprising a plurality of expert rules for selecting a therapeutic treatment regimen for the disease; and a third knowledge base comprising advisory information useful for the treatment of a patient with different constituents of the different therapeutic treatment regimens; and (b) generating in the computing device a listing (preferably a ranked listing) of therapeutic treatment regimens for the patient; and (c) generating in the computing device advisory information for one or more treatment regimens in the listing based on the patient information and the expert rules.

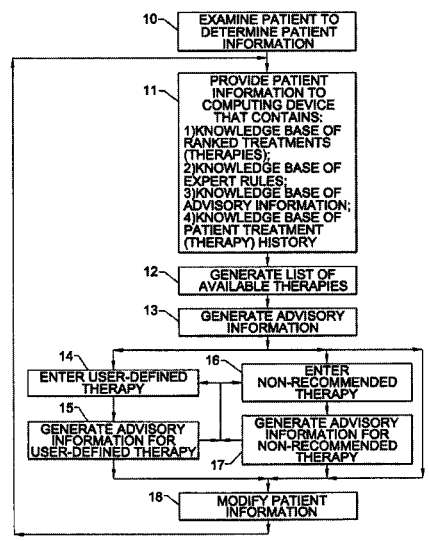

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–66 is confirmed.

* * * * *